(12) United States Patent
Adam et al.

(10) Patent No.: US 12,173,241 B2
(45) Date of Patent: Dec. 24, 2024

(54) WASTE PLASTIC BASED OIL UPGRADING INTO HIGH VALUE CHEMICALS VIA DIRECT CATALYTIC CRACKING

(71) Applicant: TotalEnergies OneTech Belgium, Seneffe (BE)

(72) Inventors: Cindy Adam, Wierde (BE); Delphine Minoux, Nivelles (BE); Walter Vermeiren, Houthalen (BE); Geoffrey De Weeze, Blaton (BE); Nikolaï Nesterenko, Nivelles (BE)

(73) Assignee: TotalEnergies OneTech Belgium, Seneffe (BE)

( * ) Notice: Subject to any disclaimer, the term of this patent is extended or adjusted under 35 U.S.C. 154(b) by 71 days.

(21) Appl. No.: 17/917,483

(22) PCT Filed: Apr. 6, 2021

(86) PCT No.: PCT/EP2021/058964
§ 371 (c)(1),
(2) Date: Oct. 6, 2022

(87) PCT Pub. No.: WO2021/204818
PCT Pub. Date: Oct. 14, 2021

(65) Prior Publication Data
US 2023/0416612 A1    Dec. 28, 2023

(30) Foreign Application Priority Data

Apr. 7, 2020  (EP) .................................... 20168565
Apr. 7, 2020  (EP) .................................... 20168566
(Continued)

(51) Int. Cl.
*C10G 65/12*    (2006.01)
*B01J 20/08*    (2006.01)
(Continued)

(52) U.S. Cl.
CPC .............. *C10G 65/12* (2013.01); *B01J 20/08* (2013.01); *B01J 23/755* (2013.01); *B01J 23/883* (2013.01);
(Continued)

(58) Field of Classification Search
None
See application file for complete search history.

(56) References Cited

U.S. PATENT DOCUMENTS

2016/0264874 A1 *  9/2016  Narayanaswamy ..... C10G 1/10
2016/0264885 A1 *  9/2016  Narayanaswamy .... C10B 53/07
(Continued)

FOREIGN PATENT DOCUMENTS

CN    101845323 A    9/2010
CN    103980938 A    8/2014
(Continued)

OTHER PUBLICATIONS

International Search Report for PCT/EP2021/058964 dated Jun. 29, 2021.
Written Opinion for PCT/EP2021/058964 dated Jun. 29, 2021.

*Primary Examiner* — Tam M Nguyen
(74) *Attorney, Agent, or Firm* — Sughrue Mion, PLLC

(57) ABSTRACT

A process to produce olefins including: (a) Providing a hydrocarbon stream containing at least 10 wt % of pyrolysis plastic oil; (b) Optionally contacting the effluent obtained in step a) with silica gel, clays, alkaline or alkaline earth metal oxide, iron oxide, ion exchange resins, active carbon, active aluminium oxide, molecular sieves, alkaline oxide and/or porous supports containing lamellar double hydroxide modified or not and silica gel, or any mixture thereof; (c) performing a selective hydrogenation step; (d) contacting the stream obtained in step c) with a cracking catalyst to crack the olefins and/or paraffins into olefins having 2 to 4 carbon atoms (e) separating from the effluents obtained at
(Continued)

the step d) a first stream containing olefins and saturated hydrocarbons having at most 3 carbon atoms, and a second stream containing hydrocarbons having 4 or more carbon atoms and (f) recovering from said first stream the ethylene and propylene.

20 Claims, 3 Drawing Sheets

(30) Foreign Application Priority Data

| Apr. 7, 2020 | (EP) | ..................................... 20168568 |
| Apr. 7, 2020 | (EP) | ..................................... 20168569 |
| Apr. 7, 2020 | (EP) | ..................................... 20168570 |

(51) Int. Cl.

| B01J 23/755 | (2006.01) |
| B01J 23/883 | (2006.01) |
| B01J 35/61 | (2024.01) |
| C07C 4/04 | (2006.01) |
| C10G 1/00 | (2006.01) |
| C10G 1/10 | (2006.01) |
| C10G 11/18 | (2006.01) |
| C10G 31/08 | (2006.01) |
| C10G 33/00 | (2006.01) |
| C10G 45/08 | (2006.01) |
| C10G 45/10 | (2006.01) |
| C10G 45/40 | (2006.01) |
| C10G 45/44 | (2006.01) |
| C10G 65/06 | (2006.01) |
| C10G 67/06 | (2006.01) |
| C10G 67/14 | (2006.01) |
| C10G 69/06 | (2006.01) |
| C10G 69/10 | (2006.01) |

(52) U.S. Cl.
CPC ............... *B01J 35/615* (2024.01); *C07C 4/04* (2013.01); *C10G 1/002* (2013.01); *C10G 1/10* (2013.01); *C10G 11/18* (2013.01); *C10G 31/08* (2013.01); *C10G 33/00* (2013.01); *C10G 45/08* (2013.01); *C10G 45/10* (2013.01); *C10G 45/40* (2013.01); *C10G 45/44* (2013.01); *C10G 65/06* (2013.01); *C10G 67/06* (2013.01); *C10G 67/14* (2013.01); *C10G 69/06* (2013.01); *C10G 69/10* (2013.01); *C10G 2300/1003* (2013.01); *C10G 2300/104* (2013.01); *C10G 2300/201* (2013.01); *C10G 2300/202* (2013.01); *C10G 2300/4006* (2013.01); *C10G 2300/4012* (2013.01); *C10G 2300/4018* (2013.01); *C10G 2300/70* (2013.01); *C10G 2300/807* (2013.01); *C10G 2400/20* (2013.01); *C10G 2400/30* (2013.01)

(56) References Cited

U.S. PATENT DOCUMENTS

| 2019/0161683 | A1* | 5/2019 | Narayanaswamy | ... C10G 69/14 |
| 2019/0367428 | A1* | 12/2019 | Ramamurthy | ............ C07C 4/06 |
| 2023/0220282 | A1* | 7/2023 | Abbott | ................... C10G 45/26 |
| | | | | 585/241 |
| 2023/0272292 | A1* | 8/2023 | Weiss | ..................... C10G 67/04 |
| | | | | 585/241 |
| 2023/0287282 | A1* | 9/2023 | Adam | ..................... B01J 35/615 |
| 2023/0323222 | A1* | 10/2023 | Kim | ....................... C10G 45/02 |
| 2024/0043759 | A1* | 2/2024 | Ristic | ...................... C10G 9/16 |

FOREIGN PATENT DOCUMENTS

| CN | 104726134 A | 6/2015 |
| JP | 10-310778 A | 11/1998 |
| WO | 2018/127813 A1 | 7/2018 |

* cited by examiner

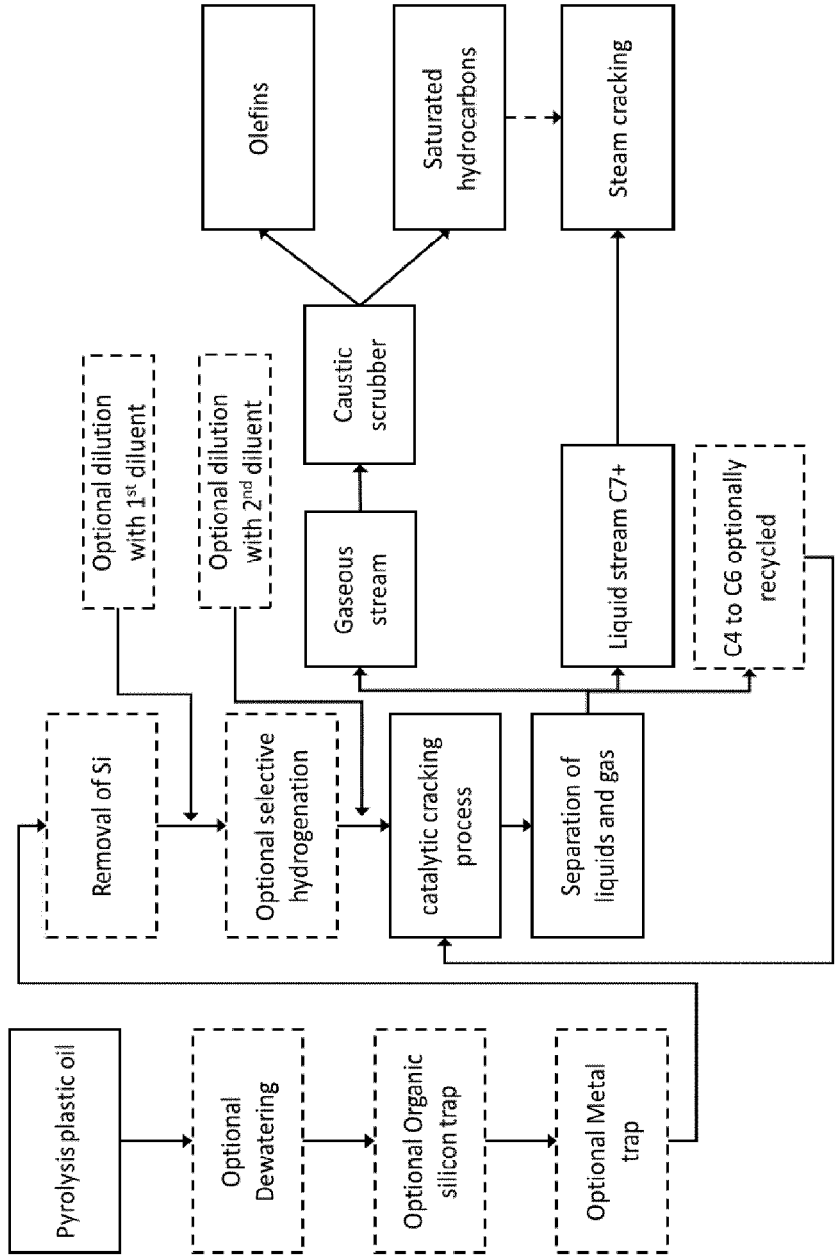

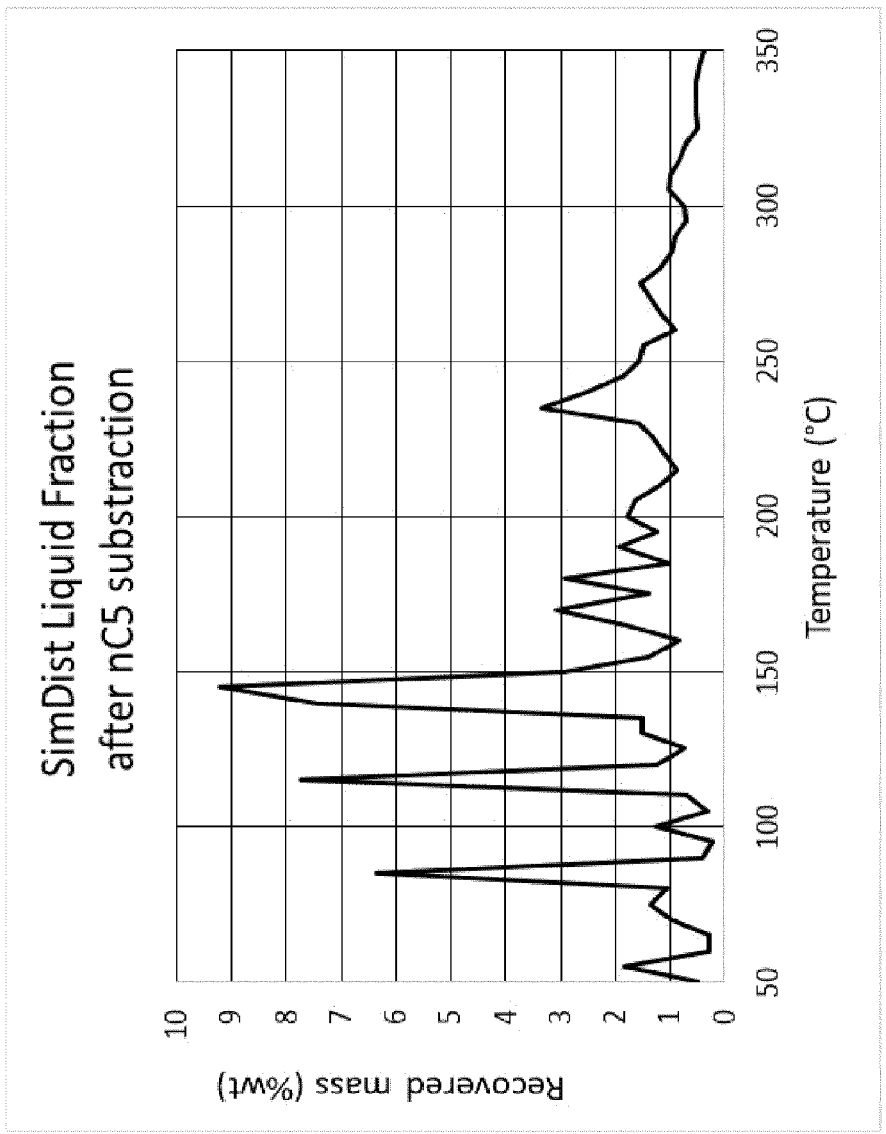
Figure 2. simulated distillation of the remaining liquid product after the catalytic test of example 1 (after substraction of the n-C5 contribution)

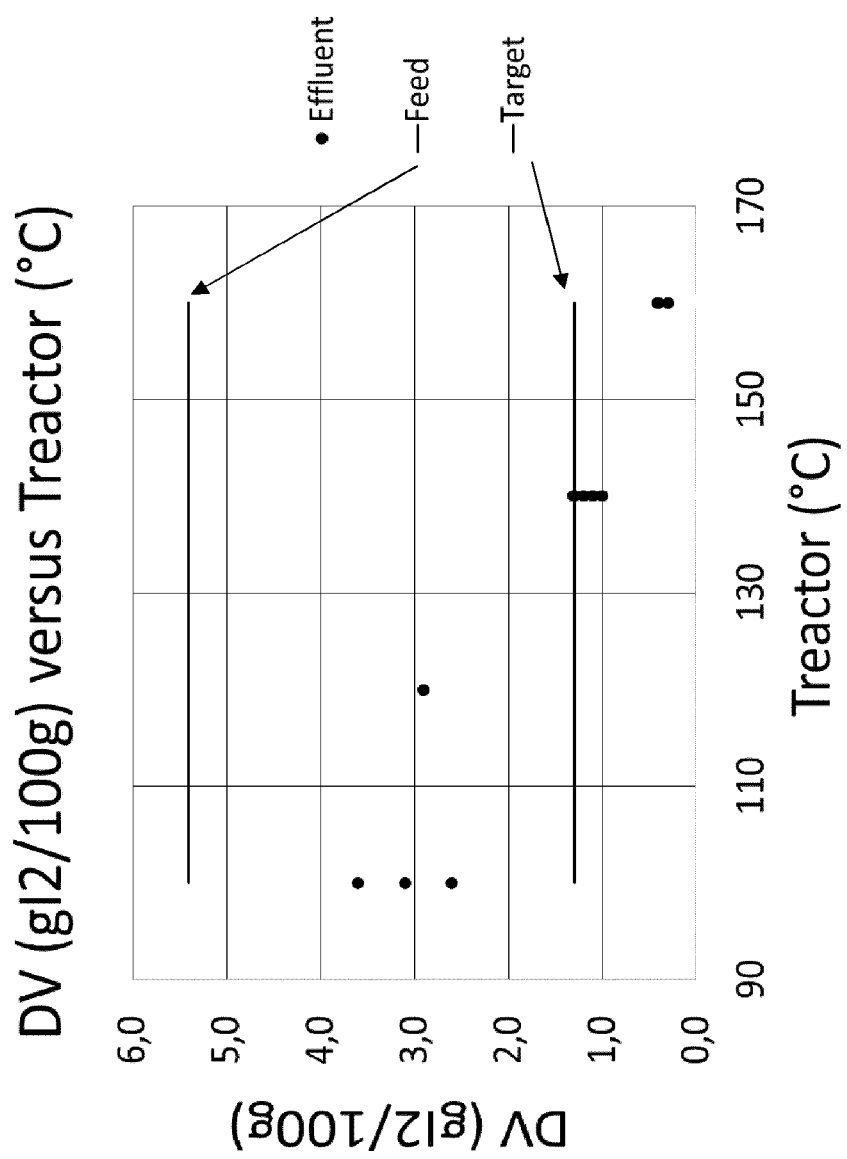
Figure 3: diene value as funtion of the temperature of the test in the case of example 3.

WASTE PLASTIC BASED OIL UPGRADING INTO HIGH VALUE CHEMICALS VIA DIRECT CATALYTIC CRACKING

CROSS REFERENCE TO RELATED APPLICATIONS

This application is a National Stage of International Application No. PCT/EP2021/058964 filed Apr. 6, 2021, claiming priority based on European Patent Application No. 20168570.8 filed Apr. 7, 2020, European Patent Application No. 20168565.8 filed Apr. 7, 2020, European Patent Application No. 20168566.6 filed Apr. 7, 2020, European Patent Application No. 20168568.2 filed Apr. 7, 2020, and European Patent Application No. 20168569.0 filed Apr. 7, 2020.

FIELD OF THE DISCLOSURE

The disclosure relates to a process for converting pyrolysis plastic oil plastic into high value chemical via catalytic cracking of the olefinic fraction and of the paraffinic fraction of the pyrolysis plastic oil.

BACKGROUND OF THE DISCLOSURE

Waste plastics are mostly diverted to landfills or are incinerated, with a smaller fraction being diverted to recycling. There is however a strong need, influenced by the regulations to limit waste plastic in landfills. On the other hand, waste plastics disposal into landfills is becoming increasingly difficult. There is therefore a need for recycling waste plastic.

Chemical recycling aims to convert plastic waste into chemicals. It is a process where the chemical structure of the polymer is changed and converted into chemical building blocks including monomers that are then used again as a raw material in chemical processes.

There are four methods of chemical recycling, which are substantially different in terms of waste input and obtained products:
- Depolymerisation turns mono-stream plastic (only feasible for condensation-type polymers, such as polyesters (notably PET) and polyamides, through hydrolysis or glycolysis) back into monomers or intermediates, which can be re-polymerised into virgin products.
- Solvent extraction (dissolution) is used to extract certain polymers using solvents without breaking down the polymer. Any colourants, additives and non-target material are removed by the selective dissolution and the resulting polymer can be reprocessed. Sometimes, it can be used for disassembling multi-layer materials.
- Pyrolysis converts mixed plastics into gas, liquid oil and solid residue char. The liquid can be further refined for fuel or new plastics production.
- Gasification is able to process unsorted, uncleaned plastic waste and turn it into syngas, which can be used to build liquid intermediates (methanol, ethanol, naphtha, . . . ) feedstocks for making base chemicals as building blocks for new polymers.

The different feedstock recycling methods require each specific feedstock requirements and produce each different product values. Gasification requires least pre-treatment amongst these three methods, followed by pyrolysis methods (thermal and catalytic cracking). Intensive pre-treatment is required in case of depolymerisation.

The low recycling rate stems from the fact that emphasis is mostly on mechanical recycling that is suitable only for homogenous and contaminant free plastic waste, which most of the plastic wastes streams are not. Post-consumers waste, end-of-life vehicles, wastes from construction and demolition, and waste electrical and electronic equipment contain large share of plastics that cannot be recycled via mechanical routes.

Chemical recycling through gasification or pyrolysis still have several hurdles. Firstly, gasification plants are very capital intensive, requires a subsequent syngas conversion unit and hence need to be built at large scale to benefit from economy of scale, which means that large waste streams need to be secured to the plant (implying logistical costs, risk of fluctuating flowrates and varying compositions of the syngas). Pyrolysis can often be justified at smaller scale while the multiple liquid product streams can be further processed in centralized plants. Even though pyrolysis can handle any type of organic material, non-organic materials like metals, glass fibres, halogens, additives and often hetero-atomic containing polymers, like PET and PVC, it remains necessary to remove the impurities from the input stream, ideally before the process or through purification of the pyrolysis oil afterwards.

Pyrolysis and gasification transform plastics, and most of their additives and contaminants into vaporous chemicals while most of the non-volatile contaminants or additives end up in the solid by-product, chars or ashes respectively. In principle, any kind of plastic waste can be converted, although some pre-sorting of non-organic waste is desired and purification of the output material is necessary as some unwanted elements can be present (for instance chlorine, silicon, metals, phosphorous, nitrogen, and other elements.

On the other hand, plastic waste is a complex and heterogeneous material, due to several factors. First, plastic as material refers to numerous different polymers with different chemical properties that need to be separated from each other prior to recycling. The main polymers found in plastic from municipal solid waste are polyethylene terephthalate (PET), polyethylene (PE), polypropylene (PP) and polystyrene (PS). Others are polyurethanes, polyamides (Nylons) and polycarbonates or polyesters.

Second, many different additives are being introduced during the production phase to adjust or improve the properties of the plastic or to fulfil specific requirements. These include additives such as functional additives (stabilisers, antistatic agents, flame retardants, plasticizers, lubricants, slip agents, curing agents, foaming agents, biocides, antioxidants etc.), colourants, fillers, commonly used in plastic packaging as well as additives such as flame retardants, commonly used in plastic for electronics. Additionally, several metal compounds are purposely added during plastic production (often as oxides, acids, etc.). Beside metals other hetero-elements additives are used in making plastics, for instance in flame retardants, plasticisers, stabilisers etc.

Silicon containing organics are used often in plastic formulations. Thanks to their surface characteristics, applications for silicones range from silicone rubbers, used as sealants for joints, to silicone surfactants for cosmetic products while they are increasingly used in the plastics sector, as process enhancing additives (processing aids), and for the modification of polymers.

On top of these hetero-elements, the used waste plastics can have been contaminated during use by sticking residuals of contained liquids (beverages, personal-care products, etc) and of food that can also introduce contamination of the plastic.

Hence it is possible that pyrolyzed plastic oil contains other components such as halogenated compounds, alkali metals, phosphorous compounds, or even iron.

In the particular case of halogenated compounds, halogenate (mainly chlorine —Cl) is mainly coming either from PVC (polyvinylchlorides), or from other plastic additives (entering in the composition of flame retardants or secondary plasticizers for example). The organic chlorides may lead to the formation of HCl in downstream processes, which can cause corrosion of equipment and may also act as a poison for catalysts used in the downstream processes.

Ammonium chloride is formed by reaction of HCl with traces of ammonia formed during pyrolysis. At high temperatures, it is not an issue because the ammonium chloride readily dissociates into HCl and NH3 but once temperatures in sections of the plant drops below 100° C., at atmospheric pressure, the compound is stable as NH4Cl and deposits onto equipment.

In the particular case of alkali metals, elements like sodium (Na) can be present. Typical sources of sodium include a malfunctioning washing step, sea water contamination or caustic contamination. Sodium is found in plastic additives (porogen or blowing agents, thermal stabilizers, . . . ) as well. In addition to Na, calcium (Ca) may also be present. Ca can be found in plastic additives (mineral fillers, thermal stabilizers, etc.).

Phosphorus compounds are often found to originate from injection of corrosion inhibitors or flame retardants in the form of thiophosphorus compounds like thiophosphate esters, thiophosphites and tributyl phosphate or organophosphates such as triphenyl phosphate (TPP), resorcinol bis (diphenylphosphate), bisphenol A diphenyl phosphate, and tricresyl phosphate; phosphonates such as dimethyl methylphosphonate; and phosphinates such as aluminium diethyl phosphinate or compounds containing both phosphorus and a halogen. Such compounds include tris(2,3-dibromopropyl) phosphate (brominated tris) and chlorinated organophosphates such as tris(1,3-dichloro-2-propyl)phosphate and tetrakis(2-chlorethyl) dichloroisopentyldiphosphate. Phosphorus compounds are also found as plastics additives as plasticizers.

Iron (Fe) originates from rust and iron scale from corrosion of upstream equipment, as well as from unfiltered particulates present in the feed. In plastics, iron oxides as well as other oxides of metallic salts can be added as insoluble pigments that colour or opacify plastics, or as mineral fillers. Iron carboxylate, like naphthenates can form from corrosion due to organic acids, like terephthalic acids or naphthenic acid in the feed, and the iron readily precipitates out in the presence of heat, water and H2S. Currently very limited knowledge exists about the fate of metals and other hetero-element containing additives during plastic pyrolysis which are often not analysed in the liquid products. During pyrolysis, the solid plastics goes through a melting phase, decomposition and volatilization. The vapours are condensed forming a liquid product and the gases separated. Some solid residue remains. Hetero-element containing volatiles can end up in the gases (e.g. HCl, NH3 etc) or in the liquid product (chloro-aromatic, bromo-aromatics, phenols, carboxylic aromatics, alkyl-amines etc). During pyrolysis at increased temperature, silicones can convert into volatile siloxanes, having boiling points similar to naphtha components.

Finally, pyrolysis of waste plastics allows to produce naphtha, ethylene, propylene and aromatics. But those products are polluted by many hetero elements originating from the waste plastic itself. Significant concentration of silicon and of organic silicon can be found in the pyrolysis plastic oils. Many attempts were focused on the removal of chlorine compounds. In particular, WO2015/026592 describes a method for processing hydrocarbons wherein a hydrocarbon stream including chlorides from one or more of a crude, vacuum or coker column is contacted with an adsorbent capable of adsorbing the chlorides in an adsorbent bed to provide a dechlorinated hydrocarbon stream to a hydrotreater reactor.

U.S. Pat. No. 6,743,746 (B1) describes a catalyst used in the low-temperature pyrolysis of hydrocarbon-containing polymer materials and being mainly intended for use in the recycling of rubber waste materials. The catalyst is prepared from a carbon-iron component in the form of microscopic carbon particles and ultra-dispersed iron particles.

EP0823469 discloses the pyrolysis of waste plastic including vinyl chlorine in which the dechlorination is firstly performed prior to the pyrolysis process.

WO2014040634 describes plastic wastes which for at least 80 wt-% contain a polymer or a mixture of polymers from a group including polymethyl methacrylate, polypropylene, polyethylene, polystyrene, polyethylene terephthalate and/or polytetrafluoroethylene, are recycled using the following steps: (i) heating the plastic wastes to a temperature at which they are flowable; (ii) pyrolyzing the flowable plastics together with a catalyst and/or an adsorber and withdrawing the resulting gases; (iii) condensing the gases.

US2005165262 describes a low energy method of pyrolysis of rubber or other hydrocarbon material. The hydrocarbon material is heated while maintaining a vacuum, using a clay catalyst.

WO2018025103 describes a process for dechlorination of a hydrocarbon stream comprising the introduction of the hydrocarbon stream together with a first zeolitic catalyst and with a stripping gas to a devolatilization extruder (DE) to produce an extruder effluent. The hydrocarbon stream comprises one or more chloride compounds in an amount of equal to or greater than about 10 ppm chloride, based on the total weight of the hydrocarbon stream and the extruder effluent comprises one or more chloride compounds in an amount of less than the chloride amount in the hydrocarbon stream.

WO2018025104 describes a process for processing mixed plastics comprising simultaneous pyrolysis and dechlorination of the mixed plastics, the process comprising contacting the mixed plastics with a zeolitic catalyst in a pyrolysis unit to produce a hydrocarbon product comprising a gas phase and a liquid phase; and separating the hydrocarbon product into a hydrocarbon gas stream and a hydrocarbon liquid stream, wherein the hydrocarbon gas stream comprises at least a portion of the gas phase of the hydrocarbon product, wherein the hydrocarbon liquid stream comprises at least a portion of the liquid phase of the hydrocarbon product, wherein the hydrocarbon liquid stream comprises one or more chloride compounds in an amount of less than about 100 ppmw chloride, based on the total weight of the hydrocarbon liquid stream, and wherein the hydrocarbon liquid stream is characterized by a viscosity of less than about 400 cP at a temperature of 300° C.

WO 2018/127813 describes a process for producing propylene and cumene comprising converting plastics to hydrocarbon liquid and pyrolysis gas in pyrolyzer; feeding hydrocarbon liquid to hydro processor to yield hydrocarbon product and first gas stream; introducing hydrocarbon product to second separator to produce first C6 aromatics and refined product; feeding refined product to steam cracker to produce steam cracker product; introducing steam cracker product to third separator to produce second C6 aromatics, third propylene stream, second C2-C4 unsaturated stream, C1-4 saturated gas, and balance hydrocarbons product; introducing pyrolysis gas and/or first gas stream to first separator to produce first propylene stream, first C2-C4 unsaturated stream, and saturated gas stream; feeding first and/or second C2-C4 unsaturated stream to metathesis reactor to produce second propylene stream; feeding first and/or second C6 aromatics, and first, second, and/or third propylene stream to alkylation unit to produce cumene; and conveying balance hydrocarbons product to pyrolyzer and/or hydro processor.

CN 101 845 323 discloses a process for producing petrol and diesel oil by plastic oil. The plastic oil is used as raw materials to be distilled through catalytic reaction, and then, the hydrogenation refining is carried out for producing high-quality petrol and diesel oil. The process comprises firstly, a step of obtaining petrol and diesel oil distillate from the plastic oil through catalytic reaction distillation; then, selecting the hydrogenation reaction of the petrol and diesel oil distillate under the mild conditions on the metal (noble metal or non-noble metal) catalysts to remove diolefines; next, carrying out hydrogenation refining reaction on the sulphide catalysts; removing monoene compounds through monoene hydrogenation saturation reaction; and carrying out desulfurization, denitrification and colloid removal production to obtain extraneous-odor-free and high-quality petrol and diesel oil.

CN 104 726 134 discloses a method for producing high-quality gasoline/diesel from chlorine-containing plastic oil, belonging to the technical fields of environmental protection and energy. The method is characterized by comprising the following steps: injecting chlorine-containing plastic oil into a high-temperature dechlorination tower filled with active alumina to perform high-temperature dechlorination, spraying a small amount of NaOH water solution on the top of the high-temperature dechlorination tower, and sending the dechlorinated plastic oil into a catalytic distillation tower filled with a molecular sieve/alumina catalyst to perform reaction and rectification; and pressurizing the plastic oil subjected to catalytic distillation into a hydrofining tower, distilling the hydrofined distillate oil under normal pressure, cutting into gasoline and diesel according to the recovered temperature, and mixing the tower bottom heavy oil and the raw material chlorine-containing plastic oil to react.

JP H10 310778 discloses how to purify an oil made from waste plastics into a high-quality automotive fuel oil using a fluid catalytic cracking unit without the use of hydrogen where 1-100 vol. % of an oil made from waste plastics and containing dienes, chlorine and oxygen is mixed with a petroleum fraction >=250 deg. C. in boiling point, and the resultant mixture is subjected to a fluid catalytic cracking unit.

CN 103 980 938 discloses a method for producing a clean fuel by adopting chlorine-containing plastic oil, and belongs to the fields of environmental protection and energy technologies. The method is characterized by comprising the steps of injecting the chlorine-containing plastic oil into a catalytic distillation tower filled with a molecular sieve/alumina catalyst for reaction and rectification; performing heat exchange on the chlorine-containing plastic oil after catalytic cracking, feeding the chlorine-containing plastic oil after heat exchange into a low-pressure liquid phase hydrogenation tower, and performing hydrogenation and dechlorination, wherein the used catalyst is a supported metal catalyst; feeding the distillate oil after the liquid phase hydrogenation into a washing tower, circulating the aqueous phase of the lower layer at the tower bottom, compressing the washed distillate oil of the upper layer, feeding the distillate oil into a hydrofining tower, hydrofining with a sulfide catalyst, removing monoene compounds through monoene hydrogenation saturation reaction, removing sulfur, nitrogen and colloids to obtain mixed gasoline and diesel oil without peculiar smell and with high quality, distilling to obtain distillate oil of gasoline and diesel oil, and mixing the heavy oil at the tower bottom and the chlorine-containing plastic oil serving as a raw material for reacting again.

US2016264874 describes an integrated process for the conversion of waste plastics to high value products. The process allows for operation with a single hydroprocessing reactor which provides simultaneous hydrogenation, dechlorination, and hydrocracking of components of a hydrocarbon stream to specifications which meet steam cracker requirements, with the option to further dechlorinate the treated hydrocarbon stream in a polishing zone.

The above described processes are mainly focused on the removal of chlorine impurities. There are however other impurities in the pyrolysis plastic oil that simply forbid the direct use of pyrolysis plastic oil in other processes like the steam cracker. Indeed, the steam cracker is very sensitive to the presence of olefins or of dienes, of compound with hetero-atoms and also to the presence of silicon or of organic silicon compounds. There is therefore a need for an improved process for the purification of pyrolysis plastic oil before using it in other process like in steam cracker.

In some other cases, the pyrolysis plastic oil is hydrogenated or hydrocracked before being further used as gasoline or treated in a steam cracker. Those treatments require high quantities of hydrogen and high operational costs due to high pressure required. To have those process competitive, it is therefore necessary to find other process requiring less hydrogen and lower pressure.

SUMMARY OF THE DISCLOSURE

The aim of the present disclosure is to provide an upgraded stream originating from the pyrolysis of plastic wastes. In particular, the aim is to upgrade pyrolysis plastic oil into olefins such as ethylene and propylene. In a preferred embodiment, part of the upgraded stream containing paraffin is further used in steam cracking process in order to produce olefins and aromatics that can be further used to produce plastic.

The disclosure relates to a process to produce olefins from a hydrocarbon stream comprising pyrolysis plastic oil comprising the following steps:
  a) Providing a hydrocarbon stream containing at least 10 wt % of pyrolysis plastic oil preferably 25 wt %, even more preferably 50 wt %, even more preferably 75 wt % of pyrolysis plastic oil the other part of said hydrocarbon stream being a first diluent or alternatively providing a hydrocarbon stream containing only pyrolysis plastic oil;
  b) Optionally putting in contact the effluent obtained at the step a) with silica gel, clays, alkaline or alkaline earth metal oxide, iron oxide, ion exchange resins, active carbon, active aluminium oxide, molecular sieves, alkaline oxide and/or porous supports containing lamellar double hydroxide modified or not and silica gel, or any mixture thereof to trap silicon and/or metals and/or phosphorous and/or halogenates trap and/or water;
  c) performing a selective hydrogenation step at a temperature ranging from 25 to 225° C. preferably 200° C., a LHSV ranging from 1 to 10 h−1, a pressure ranging from 5 to 90 barg so that the effluent obtained at the exit of said selective hydrogenation step has preferably a diene value of at most 2.0 gI2/100 g even preferably at most 0.5 gI2/100 g as measured according to UOP 326 d) contacting the stream obtained at the step c), being preferably diluted with a second diluent, with a cracking catalyst being a 10 MR and/or 12 MR molecular sieve at a temperature ranging from 450° C. to 650° C., a total pressure ranging from 0.5 to 10 barg and/or with an hydrogen partial pressure ranging from 0 to 7.5 barg to crack the olefins and/or paraffins of said pyrolysis plastic oil into olefins having 2 to 4 carbon atoms e) separating from the effluents obtained at the step d) a first stream containing olefins and saturated hydrocarbons having at most 3 carbon atoms, and a second stream containing hydrocarbons having 4 or more carbon atoms f) recovering from said first stream the ethylene and propylene.

The disclosure is further remarkable in that one or more of the following statements is true:

said pyrolysis plastic oil in said hydrocarbon stream has a starting boiling point of at least 15° C., and a final boiling point of at most 700° C., preferably at most 600° C. even more preferably 560° C., more preferably 450° C. even more preferably 350° C., the most preferred 250° C., and/or said pyrolysis plastic oil has a diene value of at least 1.0, preferably 1.5, preferably 2, even more preferably 5 gI2/100 g, to at most 50 gI2/100 g as measured according to UOP 326, and/or contains more than 2 ppm wt of metals and/or said hydrocarbon stream contains preferably at least 25 wt %, more preferably at least 50 wt %, even more preferably at least 75 wt % of said pyrolysis plastic oil and preferably at most 80 wt % of pyrolysis plastic oil, and/or at most 90 wt % preferably at most 95 wt %, even more preferably at most 100 wt % of said pyrolysis plastic oil or alternatively providing a hydrocarbon stream containing only pyrolysis plastic oil and/or said pyrolysis plastic oil comprises at least 5 ppm wt of Si to preferably at most 5000 ppm wt, and/or at least 1 ppm wt of Cl to preferably at most 5000 ppm wt, and/or at least 1 ppm wt of P to preferably at most 5000 ppm wt based on the total weight of said pyrolysis plastic oil said pyrolysis plastic is originating directly, i.e. without further treatment or modification, from a waste plastic pyrolizer where waste plastic have been thermally pyrolyzed or alternatively said pyrolysis plastic oil and/or said hydrocarbon stream of step a) is treated before step b) in one or more of the followed pre-treatment unit:

In a desalting unit to remove water-soluble salts

In an impurities removal treatment step to remove silicon, phosphorous, metals and/or halogenated compounds, via preferably a solvent extraction or preferably in a guard bed, said guard bed preferably working at a temperature of at most 200° C., and/or a LHSV between 1 to 10 h−1, and/or a pressure ranging from 1 to 90 barg either in presence of H2 or in the absence of H2

In a separation unit to extract the particles and gums by filtration, centrifugation or a combination of the two technics; and/or In a dewatering unit to remove water in said hydrocarbon stream to reach a water content of less than 0.1% vol preferably of less than 0.05% vol according to ASTM D95.

said first diluent is selected from an olefinic or paraffinic refinery or petrochemical stream including butenes, pyrolysis gasoline from a steam cracker, light cracked naphtha spirit from a FCC, coker naphtha from a coker, or a saturated hydrocarbon, having a boiling range from 15 to 250° C., preferably 75 to 200° C., as measured with method ASTM D2887, preferably said first diluent is part of said second stream recovered at step e) or any combination thereof.

the weight concentration of said pyrolysis plastic oil in said hydrocarbon stream at the inlet of the catalytic cracking step d) is chosen so that the total content of olefins in said hydrocarbon stream is at most 60 wt %, preferably at most 55 wt %, most preferably at most 50 wt % more preferably 20 wt %, even more preferably at most 15 wt %, the most preferably at most 10 wt %.

said trap of step b) is a silica gel, activated carbon, activated aluminium oxide and/or molecular sieves working at a temperature ranging from 20 to 200° C. and/or a LHSV between 1 to 10 h−1, and/or a pressure ranging from 1 to 90 barg preferably in presence of H2 or in absence of H2.

in said hydrocarbon stream at least 10 wt %, preferably 15 wt. %, preferably at least 25 wt. %, even more preferably at least 50 wt. % of said hydrocarbon stream based on the total weight of said hydrocarbon stream has an initial boiling point of at least 150° C. based on the total weight of said hydrocarbon stream.

concerning said selective hydrogenation step of said hydrocarbon stream, one or more of the following statements is true:

The LHSV ranges from 1 to 6 h−1, preferably from 2 to 4 h−1,

The pressure ranges from 15-50 barg or preferably from 25 to 40 barg in presence of H2, and/or the molar ratio of H2 to the total molar sum of alkynes and dienes in said hydrocarbon stream is of at least 1.5, preferably at least 2, most preferably at least 3 to at most 15

Said selective hydrogenation step is performed in one or more catalyst bed with preferably an overall temperature increase of at most 150° C., more preferably of at most 100° C., and/or a temperature increase of at most 100° C., more preferably of at most 50° C. for each catalyst bed, with preferably intermediary quench between said catalyst beds, said quench being preferably performed with H2 or with the effluents of said selective hydrogenation step said first step is performed in a fixed bed reactor preferably over a catalyst that comprises at least one metal of group VIII, preferably selected from the group of Pt, Pd, Ni and/or mixture thereof on a support such as alumina, titania, silica, zirconia, magnesia, carbon and/or mixtures thereof; preferably said catalyst is a Ni based catalyst being a passivated after its reduction using preferably di-alkyl-sulfide such as DiMethylSulfide (DMS) or DiEthylSulfide (DES) or thiophenic compounds.

said first step can also be performed in a fixed bed reactor preferably over a catalyst that comprises at least one metal of group VIB as for example Mo, W in combination or not with a promotor selected from at least one metal of group VIII and/VIIIB as for example Ni and/or Co, and/or mixture thereof, these metals being used in sulfided form and preferably supported on alumina, titania, zirconia, silica, carbon and/or mixtures thereof the effluents obtained at the exit of said selective hydrogenation step has a diene value of at most 1.5 gI2/100 g, preferably at most 1.0 gI2/100 g even more preferably at most 0.5 gI2/100 g.

Concerning said step d) of contacting the stream obtained at the previous step with a cracking catalyst, one or more of the following statements is true:

temperature of cracking reaction ranges from 500 to 650° C., more preferably from 520 to 600° C., yet more preferably from 540 to 580° C., typically around 560° C. to 580° C.;

the cracking reaction is performed in a fixed bed reactor, or a moving bed reactor or a fluidized bed reactor;

the LHSV ranges from 1 to 30 h−1, preferably from 5 to 20 h−1, more preferably from 5 to 15 h−1

The total pressure in the reactor ranges from 0.5 to 10 barg, preferably from 0.5 to 5 barg, more preferably from 0.5 to 2 barg;

The cracking reaction is performed without hydrogen or hydrogen is present at a at a pressure of maximum 2.5 barg, preferably at a pressure of maximum 1.5 barg; preferably in presence of dimethyl di sulfur at a concentration ranging from 50 to 300 ppm wt, more preferably at a concentration of 150 ppm wt; and/or The catalyst is selected from SAPO-5, and the like having an AFI structure, SAPO-41, and the like having an AFO structure, SAPO-11, and the like having an AEL structure, structure or SAPO-37, and the like having a FAU structure with preferably a silicon content ranging from 0.1 to 10 atom %, where the sum of Al+P+Si is 100, or MFI, for instance ZSM-5, silicalite-1, boralite C, TS-1; MEL, for instance ZSM-11, silicalite-2, boralite D, TS-2, SSZ-46; FER for instance Ferrierite, FU-9, ZSM-35; MTT for instance ZSM-23; MWW for instance MCM-22, PSH-3, ITQ-1, MCM-49; TON for instance ZSM-22, Theta-1, NU-10; EUO for instance ZSM-50, EU-1; MFS for instance ZSM-57; CON like CIT-1; and ZSM-48 family of microporous materials consisting of silicon, aluminium, oxygen and optionally boron; preferably the cracking catalyst is a crystalline silicate, metal containing crystalline silicate or a dealuminated crystalline silicate or any mixture thereof; most preferably the cracking catalyst has a MFI or the MEL structure advantageously modified with the metals Mg, Ca, La, Ni, Ce, Zn, Co, Ag, Fe, Cu or Ga or mixtures thereof with a metal content preferably of at least 0.1 wt % and at most 10 wt %; preferably the cracking catalyst is a P-modified zeolite, Phosphorus-modified zeolite, preferably prepared based on MFI, MOR, MEL, clinoptilolite or FER, MWW, TON, EUO, MFS and ZSM-48 family having an initial Si/Al ratio advantageously between 4 and 500 after step e), hydrocarbons having 4 to 6 carbon atoms are separated from said second stream to be further cracked preferably by recycling them at step d).

The hydrocarbons having at least 7 carbon atoms are separated from said second stream, hydrogenated and/or hydrotreated and sent at least partially to a steam cracker to be cracked into olefins.

The process for purification comprises the preliminary step a1) of providing a waste plastic stream; a2) pyrolyzing said waste plastic stream at a temperature of at least 200° C.; a3) recovering a pyrolizer effluent and separating said pyrolizer effluent into a C1 to C4 hydrocarbons fraction, a fraction having a boiling range higher than 350° C. and a fraction being said pyrolysis plastic oil; a4) sending said fraction having a boiling range higher than 350° C. into a FCC, or an hydrocracking unit, a coker or a visbreaker or blending said fraction having a boiling range higher than 350° C. in crude oil or crude oil cut to be further refined.

said of pyrolysis plastic oil originates directly from the pyrolysis of plastic wastes without further chemical transformation or separation.

After step e), the hydrocarbons having a boiling point higher than 350° C. are removed from said second stream and are further converted into a FCC, or an hydrocracking unit, a coker or a visbreaker or blended in crude oil or in a crude oil cut to be further refined.

said second diluent is incorporated at step d) so that the olefins content at the inlet step d) is at most 60 wt %, preferably at most 55 wt %, most preferably at most 50 wt %, being and olefinic or paraffinic refinery stream, or part of said second stream recovered at step e), even more preferably said second diluent is a naphtha having a boiling range from 15 to 250° C., preferably 38 to 150° C., as measured with method ASTM D2887 or a saturated hydrocarbon solvent, having a boiling range from 15 to 250° C., preferably 75 to 200° C., as measured with method ASTM D2887, preferably being N-pentane or iso-paraffinic solvent, or any mixture thereof a guard bed to trap solid particles is located on the top of said selective hydrogenation step said hydrocarbon stream contains only pyrolysis plastic oil or alternatively said hydrocarbon stream contains at least 25 wt % preferably at least 50 wt %, even more preferably 75 wt %, even more preferably 90 wt %, of pyrolysis plastic oil the other part of said hydrocarbon stream being a first diluent The process of this disclosure is advantaging in that it does not require complex purification steps of the pyrolyzed plastic stream prior to its conversion into high value chemicals. The use of the cracking process allows to simultaneously crack and purify the pyrolysis plastic oil stream. Finally, part of the hydrocarbons obtained at the end of the inventive process can be sent to the steam cracker unit without further purification.

The process of the disclosure is also advantaging in that the catalytic cracking process does not consume H2. A H2 cover is sometimes used to avoid unwanted reactions. However, H2 is not significantly consumed. The operational costs of the process are therefore limited. The process of the disclosure also takes advantage of the presence of olefins in the pyrolysis plastic oils. Instead of hydrogenating those olefins to latter on crack the hydrocarbon obtained in a steam cracker, the olefins already present in the pyrolysis plastic oil are converted into valuable olefins such as ethylene and propylene.

Definitions

For the purpose of the disclosure, the following definitions are given:

The terms "alkane" or "alkanes" as used herein describe acyclic branched or unbranched hydrocarbons having the general formula $C_nH_{2n+2}$, and therefore consisting entirely of hydrogen atoms and saturated carbon atoms; see e.g.

IUPAC. Compendium of Chemical Terminology, 2nd ed. (1997). The term "alkanes" accordingly describes unbranched alkanes ("normal-paraffins" or "n-paraffins" or "n-alkanes" or "paraffins") and branched alkanes ("iso-paraffins" or "iso-alkanes") but excludes naphthenes (cycloalkanes). They are sometimes referred to by the symbol "HC—".

The terms "olefin" or "alkene" as used herein relate to an unsaturated hydrocarbon compound containing at least one carbon-carbon double bond. They are sometimes referred to by the symbol "HC=".

The terms "alkyne" as used herein relate to an unsaturated hydrocarbon compound containing at least one carbon-carbon triple bond.

The term "hydrocarbon" refers to the alkanes (saturated hydrocarbons), cycloalkanes, aromatics and unsaturated hydrocarbons together.

As used herein, the terms "C# alcohols", "C# alkenes", or "C# hydrocarbons", wherein "#" is a positive integer, is meant to describe respectively all alcohols, alkenes or hydrocarbons having # carbon atoms. Moreover, the term "C#+ alcohols", "C#+ alkenes", or "C#+ hydrocarbons", is meant to describe all alcohol molecules, alkene molecules or hydrocarbons molecules having # or more carbon atoms. Accordingly, the expression "C5+ alcohols" is meant to describe a mixture of alcohols having 5 or more carbon atoms.

Weight hourly space velocity (WHSV) is defined as the hourly weight of flow per unit weight of catalyst and liquid hourly space velocity (LHSV) is defined as the hourly volume of flow per unit of volume of catalyst.

The terms "comprising", "comprises" and "comprised of" as used herein are synonymous with "including", "includes" or "containing", "contains", and are inclusive or open-ended and do not exclude additional, non-recited members, elements or method steps. The terms "comprising", "comprises" and "comprised of" also include the term "consisting of".

The recitation of numerical ranges by endpoints includes all integer numbers and, where appropriate, fractions subsumed within that range (e.g. 1 to 5 can include 1, 2, 3, 4 when referring to, for example, a number of elements, and can also include 1.5, 2, 2.75 and 3.80, when referring to, for example, measurements). The recitation of endpoints also includes the recited endpoint values themselves (e.g. from 1.0 to 5.0 includes both 1.0 and 5.0). Any numerical range recited herein is intended to include all sub-ranges subsumed therein.

The term "conversion" means the mole fraction (i.e., percent) of a reactant converted to a product or products. The term "selectivity" refers to the percent of converted reactant that went to a specified product.

The terms "wt. %", "vol. %", or "mol. %" refers to a weight, volume, or molar percentage of a component, respectively, based on the total weight, the total volume of material, or total moles, that includes the component. In a non-limiting example, 10 grams of component in 100 grams of the material is 10 wt. % of components.

The term "naphtha" refers to the general definition used in the oil and gas industry. In particular, it refers a hydrocarbon originating from crude oil distillation having a boiling range from 15 to 250° C. as measured by ASTM D2887. Naphtha contains substantially no olefins as the hydrocarbons originates from crude oil. It is generally considered that a naphtha has carbon number between C3 and C11, although the carbon number can reach in some case C15. It is also generally admitted that the density of naphtha ranges from 0.65 to 0.77 g/mL.

The term "pyrolysis plastic oil" refers to the liquid products obtained once waste plastic have been thermally pyrolyzed. The pyrolysis process shall be understood as an unselective thermal cracking process. The pyrolysis involves the breaking of the polymer chains by heating to moderate temperatures (ca. 400-600° C.). Rather than breaking the polymer down to its original monomers, pyrolysis tends to make a range of shorter chain compounds, similar in many ways to the mixtures of hydrocarbons found in crude oil and oil products. A catalyst is sometimes used to reduce the operating temperature. The plastic being pyrolyzed can be of any type. For instance, the plastic being pyrolyzed can be polyethylene, polypropylene, polystyrene, polyesters, polyamides, polycarbonates etc. These pyrolysis plastic oils contain paraffins, i-paraffins (iso-paraffins), dienes, alkynes, olefins, naphthenes, and aromatic components. Pyrolysis plastic oil may also contain impurities such as organic chlorides, organic silicon compounds, metals, salts, sulfur and nitrogen compounds, etc. The origin of the plastic lead to pyrolysis plastic oil is the waste plastic without limitation on the origin or on the nature of the plastic. The composition of the pyrolysis plastic oil is dependent on the type of plastic pyrolyzed. It is however mainly constituted of hydrocarbons having from 1 to 50 carbon atoms and impurities.

The term Diene Value (DV) or Maleic Anhydride Value (MAV) correspond to the amount of maleic anhydride (expressed as equivalents of iodine) which will react with 100 parts of oil under specific conditions. It is a measure of the conjugated double bonds in the oil. One mole of Maleic anhydride corresponds to 1 conjugated double bond. One known method to quantify the diene is the UOP 326: Diene Value by Maleic Anhydride Addition Reaction. The term diene value (DV) refers to the analytical method by titration expressed in g of iodine per 100 g of sample. The term Maleic Anhydride value (MAV) refers to the analytical method by titration expressed in mg of Maleic acid per g of sample. There is a correlation between the MAV=DV*3,863 since 2 moles of iodine correspond to 1 mole of Maleic Anhydride.

The term bromine number corresponds to the amount of bromine in grams reacted by 100 grams of a sample. The number indicates the quantity of olefins in a sample. It is determined in grams of Br2 per 100 grams of solution (gBr2/100 g) and can be measured for instance according to the method ASTM D1159.

The term bromine index is the number of milligrams of bromine that react with 100 grams of sample. It is determined in milli grams of Br2 per 100 g of solution (mg Br2/100 g) and can be measured for instance according to the method ASTM D2710.

The term boiling point used refers to the boiling point generally used in the oil and gas industry. They are measured at atmospheric pressure. The initial boiling point is defined as the temperature value when the first bubble of vapor is formed. The final boiling point is the highest temperature that can be reached during a standard distillation. At this temperature, no more vapor can be driven over into the condensing units. The determination of the initial and the final boiling point is known per se in the art. Depending on the boiling range of the mixture they can be determine using various standardized methods such as for instance the ASTM D2887 relating to the boiling range distribution of petroleum fractions by gas chromatography. For compositions containing heavier hydrocarbons the ASTM D7169 can alternatively be used. The boiling ranges of the distillates can also advantageously be measure using the ASTM D7500.

The surface area and porous volume are measured via N2 adsorption using usual surface area measurements. In particular, surface area measurements such as "BET" measurement can be used (i.e. ASTM D3663 for the surface area and D4365 for the porous volume). Other techniques well known in the art can also be considered such as mercury adsorption techniques (ASTM D4284). All measurements and data plots as utilized herein were made with a Micromeritics® Tristar 3000® analyser. Surface Area: Total surface area was determined by N2 sorption analysis according to ASTM D 4365-95 (reapproved 2008). Pore diameter and pore volume were determined according to D4641-94 (reapproved 2006).

The concentration of metals in the matrix of hydrocarbon can be determined by any method known in the art. In particular, relevant characterization methods include XRF or ICP-AES methods. The man skilled in the art knows which method is the most adapted to each metal and to which hydrocarbon matrix.

The particular features, structures, characteristics or embodiments may be combined in any suitable manner, as would be apparent to a person skilled in the art from this disclosure, in one or more embodiments.

DESCRIPTION OF THE FIGURES

FIG. 1 describes a possible process scheme according to the disclosure. The pyrolysis plastic oil is optionally diluted and treated in a dewatering unit. It is then further treated over traps to remove silicon, metals and Ca, Mg if any. An optional low temperature hydrotreatment can be performed to remove the dienes and alkynes if any. The stream is then treated in a catalytic cracking process where the olefins and/or long chain paraffins are converted into light olefins namely ethylene and propylene. The effluent of the catalytic cracking process is then separated into a first and a second stream. The second stream being a liquid stream contains mainly C7+ and the first stream being a gaseous stream contains ethylene, propylene and also saturated hydrocarbons. Optionally the C4 to C6 are separated and recycled at the catalytic cracking unit. The second stream can be for instance sent to the steam cracking without further purifications. The gaseous stream is optionally treated over a caustic scrubber to remove the impurities such HCl, H2S and NH3. The saturated hydrocarbons of the gaseous stream can then further be cracked in a steam cracker without further purification.

FIG. 2 shows the simulated distillation of the remaining liquid product after the catalytic test of example 1 (after subtraction of the n-C5 contribution).

FIG. 3: diene value represented as function of the reaction temperature in the case of example 3.

DETAILED DESCRIPTION OF THE DISCLOSURE

With regards to the hydrocarbon stream, it can contain a first diluent. In that case, said hydrocarbon stream contains at least 10 wt % of pyrolysis plastic oil. In a preferred embodiment, said hydrocarbon stream contains at least 25 wt % of pyrolysis plastic oil, preferably at least 50 wt % of pyrolysis plastic oil, even more preferably 75 wt % of pyrolysis plastic oil, in the most preferred embodiment at least 90 wt % of pyrolysis plastic oil. It is also possible to use pure pyrolysis plastic oil. In this latter case, the hydrocarbon stream is only pyrolysis plastic oil. The other component of said hydrocarbon stream is said first diluent. This first diluent can be any diluent able to limit the temperature increase in said step c) of the selective hydrogenation.

With regards to the first diluent, it can be any olefinic or paraffinic refinery or petrochemical stream including butenes, pyrolysis gasoline from a steam cracker, light cracked naphtha spirit from a FCC, coker naphtha from a coker. It can also be any a saturated hydrocarbon, having a boiling range from 15 to 250° C., preferably 75 to 200° C., as measured with method ASTM D2887. It can also be any mixture of olefinic or paraffinic stream.

With regards to the second diluent, any type of hydrocarbon stream can be used as long as the olefinic content at the inlet step d) is at most 60 wt %, preferably at most 55 wt %, most preferably at most 50 wt %. Accordingly, said second diluent can be olefinic or paraffinic refinery or petrochemical stream. In a preferred embodiment, said second diluent can be a naphtha having a boiling range from 15 to 250° C., preferably 38 to 150° C., as measured with method ASTM D2887. The diluent may also be a saturated hydrocarbon solvent, having a boiling range from 15 to 250° C., preferably 75 to 200° C., as measured with method ASTM D2887. For instance, N-pentane or iso-paraffinic solvent taken from the grade (sane supplied by Total Fluid such as IP100, IP120, IP140 can also be chosen.

Advantageously said first diluent and said second diluent are the same. Advantageously, only said first diluent is used or only said second diluent is used. In a most preferred embodiment part of said second stream recovered at step e) is used as said first diluent and/or as said second diluent.

With regards to the optional dewatering of the hydrocarbon stream, it consists in any method known in the art to remove the water present in a hydrocarbon stream. As non-limiting examples, water can be removed by decantation followed by separation. Water can also be removed in a flash drum. The hydrocarbon stream can alternatively or in addition to the other methods described, can be treated over a desiccant like an alumina or molecular sieve. The various method described above can be used independently or in any combination.

With regards to the optional desalting step, it consists in the desalting techniques known in the art. For instance, typical desalters comprise one or more tanks into which said hydrocarbon stream and water are added. The hydrocarbon stream and water are intensively mixed to enhance the phase interface, typically upstream of the settling tank. The salts from the hydrocarbon stream are extracted via the aqueous phase.

Desalting is a water-washing operation performed because of the negative effect of salts in the downstream processes due to scale formation, corrosion, and catalyst deactivation. These salts can be found in two forms: dissolved in emulsified water droplets in the pyrolysis plastic oil, as a water-in-oil emulsion, or suspended amorphous or crystalline solids. The negative effects of these salts in downstream processes are: salt deposit formation as scales where water is vaporized and corrosion by hydrochloric acid formation from hydrolysis of magnesium and calcium chlorides at high temperatures (about 350° C.) as follows:

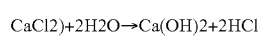

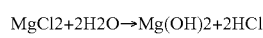

Desalting involves mixing pyrolysis plastic oil and/or said hydrocarbon stream with washing water, using a mixing valve or static mixers to ensure a proper contact between the pyrolysis plastic oil and the water, and then passing it to a separating vessel, where separation between the aqueous and hydrocarbon phases is achieved. Since emulsions can be formed in this process, there is a risk of water carryover in the organic phase. In order to overcome this problem chemical demulsifiers are added to promote the emulsion breaking or an electric field across the settling vessel is applied to coalesce the polar salty water droplets, and, therefore, separation of salty water is achieved.

In order to enhance the effective mixing between the hydrocarbon and aqueous phases and ensure the proper extraction of the salts and minerals into the aqueous phase, a mixing valve is used over which a pressure drop result in shear stress over the droplets that promotes an intimate water and oil contact. In addition to the mixing valve, upstream premixing devices can be used, such as spray nozzles or static mixers. The shear stress needs to be optimized to reach the right balance between smaller droplets, which improves the contact among the phases but however result in more stable emulsion.

Subsequently, the mixture goes to the desalter, a horizontal cylindrical tank that provides long enough residence time to separate the water and oil mixture in two phases. Some water droplets diameters are so small that they do not separate by gravity; so, an electrostatic field between two electrodes installed into the desalter is used to promote coalescence.

When emulsion is too stable and break only slowly, demulsifiers can be used. Demulsifiers are surfactants, when present at low concentration, interacts with the interfaces of the system, altering the interfacial free energies of those interfaces. In particular lipophilic anionic surfactants can be expected in the pyrolysis plastic oil, resulting from the presence of polyesters, polycarbonate and polyamides and from the presence of additives like, antioxidants and UV stabilizers, containing phenols, other oxygenated aromatics and phosphorus containing compounds and slip agents, like fatty acid amides, fatty acid esters, metallic stearates (for example, zinc stearate). An emulsion breaker will lower the interfacial tension and result in coalescence. A hydrophilic demulsifiers will balance the lipophilic surfactant.

In an embodiment, the demulsifying agent can be chosen among water, steam, acids, caustic solutions, complexing agents and their mixtures. Acids are for example strong acids, in particular inorganic acids, such as phosphoric acid, sulphuric acid. Complexing agents are for example weak organic acids (or their corresponding anhydrides) such as acetic acid, citric acid, oxalic acid, tartaric acid, malic acid, maleic acid, fumaric acid, aspartic amino acid, ethylenediaminetetraacetic acid (EDTA). Preferably, the demulsifying agent comprises water, steam, phosphoric acid, acetic acid, citric acid, oxalic acid, tartaric acid, malic acid, fumaric acid, aspartic amino acid, ethylenediaminetetraacetic acid, alkali, salts, chelating agents, crown ethers, or maleic anhydride.

With regards to the traps for silicon and/or metals and/or phosphorous and/or halogenates, it consists in silica gel, clays, alkaline or alkaline earth metal oxide, iron oxide, ion exchange resins, active carbon, active aluminium oxide, molecular sieves, and/or porous supports containing lamellar double hydroxide modified or not and silica gel, or any mixture thereof used in the fixed bed techniques known in the art. The trap is able to capture silicon and/or metals and/or phosphorous and/or halogenates, being preferably chosen among Ca, Mg, Hg via absorption and/or adsorption or it can also be constituted of one or more active guard bed with an adapted porosity. It can work with or without hydrogen coverage. The trap can be constituted of an adsorbent mass such as for instance a hydrated alumina. Molecular sieves can also be used to trap silicon. Other adsorbent can also be used such as silica gel for instance. The silicon trap is preferably able to trap organic silicon. Indeed, it is possible that the silicon present in the streams are in the form of organic silicon.

In a preferred embodiment, silicon and/or metals and/or phosphorous and/or halogenates are trapped with activated carbon. Activated carbon possesses preferably a high surface area (600-1600 m2/g), and is preferably porous and hydrophobic in nature. Those properties lead to a superior adsorption of non-polar molecules or little ionized molecules. Therefore, activated carbon can be used to reduce for instance siloxane from the liquid feed at temperature from to 150° C., at pressures from 1 to 100 bar or from vaporized feed from 150 to 400° C. at pressure from 1 to 100 bar. Regeneration of saturated adsorbent can be performed via heating while using a sweeping gas.

In a preferred embodiment, silicon and/or metals and/or phosphorous and/or halogenates are trapped with silica or silica gel. Silica gel is an amorphous porous material, the molecular formula usually as $(SiO2) \cdot nH2O$, and unlike activated carbon, silica gel possesses polarity, which is more conducive to the adsorption of polar molecules. Because of —Si—O—Si— bonds, siloxanes exhibit partial polar character, which can contribute to adsorb on silica gel surface. The adsorption force of silica gel is often weak enough allowing regeneration of silica gel by heat treatment above 150 up to 300° C. using a sweeping gas.

In a preferred embodiment, silicon and/or metals and/or phosphorous and/or halogenates are trapped with molecular sieves. Molecular sieves are hydrous aluminosilicate substance, with the chemical formula $Na2O \cdot Al2O3 \cdot nSiO2 \cdot xH2O$, which possesses a structure of three-dimensional crystalline regular porous and ionic exchange ability. Compared with silica gel, molecular sieves favour adsorption of high polarity. The regeneration of exhausted absorbents can be achieved via heating at high temperature to remove siloxane. Often, the regeneration is less efficient as the siloxanes might react irreversibly with the molecular sieve. In a most preferred embodiment, the molecular sieves are ion-exchanged or impregnated with a basic element such as Na·Na2O impregnation levels range from 3-10% wt typically and the type of sieve are typically of the A or faujasite crystal structure.

In a preferred embodiment, silicon and/or metals and/or phosphorous and/or halogenates are trapped with activated aluminium oxide. Activated aluminium oxide possesses large surface area (100-600 m2/g), which shows high affinity for siloxanes but also for polar oxide, organic acids, alkaline salts, and water. It can be an alkaline or alkaline-earth or rare-earth containing promoted alumina, the total weight content of these doping elements being less than 20% wt, the doping elements being preferably selected from Na, K, Ca, Mg, La, or mixture thereof. It can also be a metal promoted alumina where the metal is selected from group VI-B metal with hydrogenating activity such as Mo, W and/or from group VIII metal, such as Ni, Fe, Co.

Typically fresh or spent hydroprocessing alumina-supported catalysts such as those developed by Axens (ACT 971, ACT 981 and ACT 991) could be used to remove silicon compounds. The surface area and the texture of the supports as well as the formulation have been optimized to maximize the silicon removal and retention without compromising the catalyst Hydrotreating activity.

With respect to silicon removal from a feedstock, the catalyst located at the top inlet of the bed has the least hydrotreating activity and the greatest capacity for accumulating silicon compared to capacities of downstream portions of a different catalyst or catalysts beds. In the preferred embodiment wherein at least two different catalysts are employed, the catalyst located at the top of the bed has the highest capacity for collecting silicon while catalysts located downstream catalysts have diminishing silicon capacities and increasing hydrotreating activities.

In another embodiment, silicon and/or metals and/or phosphorous and/or halogenates are trapped with alkaline oxide. Alkaline oxide for high temperature treatment such as calcium oxide (CaO) has strong activity to breakdown siloxanes and can be used as non-regeneratable adsorbent at temperature between 150 and 400° C.

In another embodiment, silicon and/or metals and/or phosphorous and/or halogenates are trapped with porous supports containing lamellar double hydroxides, being preferably an hydrotalcite. The hydrotalcite can comprise one or more metals with hydrogenating capacity selected from group VIB or Group VIII, preferably Mo. Those metals can be supported on the surface of the hydrotalcite, or can have been added to the actual structure of the lamellar double hydroxide, in complete or partial substitution; as an example, but without limiting the scope of the present invention, the divalent metal, usually Mg, can be exchanged for Ni, or the trivalent metal, substituted by Fe instead of Al.

The above-mentioned solid adsorbents can be used alone or in combination in order to optimize the removal of silicon and/or metals and/or phosphorous and/or halogenates.

In another embodiment, silicon and/or metals and/or phosphorous and/or halogenates are trapped with a multi layered guard bed comprising at least two layers wherein the layer on the top of the bed is selected from silica gel, clays, alkaline or alkaline earth metal oxide, iron oxide, ion exchange resins, active carbon, active aluminium oxide, molecular sieves and wherein the layer on the bottom of the bed is selected from silica gel, clays, alkaline or alkaline earth metal oxide, iron oxide, ion exchange resins, active carbon, active aluminium oxide, molecular sieves. More preferably said layer on the top of the guard bed comprises silica gel and/or active carbon and said layer on the bottom of the guard bed comprises molecular sieves and/or active aluminium oxide.

In another embodiment, when the pyrolysis plastic oil contains high quantities of HCl and/or Halogenated compounds (namely at least 500 ppm wt of HCl based on the total amount of pyrolysis plastic oil), particular adsorbents can be used such as silica, clays—such as bentonite, hydrotalcite—alkaline or alkaline earth metal oxide—such as iron oxides, copper oxides, zinc oxide, sodium oxide, calcium oxide, magnesium oxide—alumina and alkaline or alkaline-earth promoted alumina-, iron oxide (hematite, magnetite, goethite), ion exchange resins or combination thereof. In a most preferred embodiment, silicon and/or metals and/or phosphorous and/or halogenates containing at least 500 ppm wt of HCl based on the total amount of pyrolysis plastic oil are trapped with activated alumina. As HCl is a polar molecule, it interacts with polar sites on the alumina surface such as hydroxyl groups. The removal mechanism relies predominantly on physical adsorption and low temperature and the high alumina surface area is required to maximize the capacity for HCl removal. The HCl molecules remain physically adsorbed as a surface layer on the alumina and can be removed reversibly by hot purging. Promoted aluminas are a hybrid in which a high alumina surface area has been impregnated with a basic metal oxide or similar salts, often of sodium or calcium. The alumina surface removes HCl through the mechanisms previously described, however the promoter chemically reacts with the HCl giving an additional chloride removal mechanism referred to as chemical absorption. Using sodium oxide as an example of the promoter, the HCl is captured by formation of sodium chloride. This chemical reaction is irreversible unlike physical adsorption and its rate is favored by higher temperature. The promoted alumina chloride guards are very effective for liquid feeds due to the irreversible nature and high rate of the chemical reaction once the HCl reaches the reactive site.

Another class of chemical absorbents combines Na, Zn and Al oxides in which the first two react with HCl to form complex chloride phases, for example $Na_2ZnCl_2$ and the chemical reactions are irreversible. U.S. Pat. Nos. 4,639,259 and 4,762,537 relate to the use of alumina-based sorbents for removing HCl from gas streams. U.S. Pat. Nos. 5,505,926 and 5,316,998 disclose a promoted alumina sorbent for removing HCl from liquid streams by incorporating an alkali metal oxide such as sodium in excess of 5% by weight on to an activated alumina base. Other Zn-based products range from the mixed metal oxide type composed of ZnO and Na2O and/or CaO. The rate of reaction is improved with an increase in reactor temperature for those basic (mixed) oxides.

With regards to the optional guard bed to trap solid particles, it is located on the top of said selective hydrogenation to remove the solid particles remaining in the feed such as coke particles coming from heating tubes, iron scales from corrosion, dissolved impurities such as iron, arsenic, calcium-containing compounds, sodium chloride, silicon contained in upstream additives, etc. Grading materials which have high void space to accumulate and 'store' these particulates are frequently used. Effective feed filtration to remove particulates in combination with high void grading provides a longer mitigation of pressure drop buildup. In a preferred embodiment, said guard bed to trap solid particles has a continuously decreasing particle size including a region 25 to 150 centimeters of particles, having a fraction of 0.3 to 2.0 cm diameter range. Since such guard beds to trap solid particles are designed specifically to handle the contaminants, they help to prolong the life of the hydrotreating catalyst and require fewer total catalyst changeouts.

With regards to the impurities removal treatment step to remove silicon, phosphorous, metals and/or halogenate compounds, it consists preferably of a solvent extraction unit. The solvent can be water, alcohol, NaOH, KOH, etc. For example, the silicon extraction with NaOH described in the COMET patent (EP2643432B1), the metals solvent extraction unit used in the refining of used oils.

With regards to the selective hydrogenation step, it consists mainly in the hydrogenation phase to saturate the conjugated diene and alkynes. Depending on the composition of the hydrocarbon stream, the first hydrotreating step is performed either in liquid phase or in trickle bed mode. This step is well known in steam cracking unit as $1^{st}$ step hydrogenation of pyrolysis gasoline. The selective hydrogenation step will hydrogenate the diene and in particularly the conjugated diene and acetylenic bonds. The selective hydrogenation step will lead to a decrease of the diene value. The decrease of the diene value observed between the inlet and the outlet of the selective hydrogenation step should be of at least 10% preferably at least 25% as measured according to UOP 326.

As regards the cracking catalyst of step d), it can be any acid catalyst capable to cause the cracking of the olefins and/or long chain paraffins contained in the pyrolysis plastic oil under above said conditions. The cracking catalyst preferably contains no noble metals. In particular the olefin cracking catalyst preferably contains no Pt, no Pd and no Au. By way of example, it can be: molecular sieves, modified zeolites (including P-modified zeolites), a lamellar zeolite such as ITQ-2, metal-aluminophosphates. For example, a known catalyst may be used such as a solid acid catalyst of e.g. a clay mineral such as kaolin, such as Al-MCM41, such as an aluminum phosphate The catalyst is employed under particular reaction conditions whereby the catalytic cracking of the C4+ olefins and/or C7+ paraffins readily proceeds. Different reaction pathways can occur on the catalyst. Catalytic cracking may be understood to comprise a process yielding shorter molecules via bond breakage.

In a preferred embodiment, the cracking catalyst is a crystalline Porous Aluminophosphate containing advantageously at least one 10 and/or 12 members ring into the structure.

The porous crystalline aluminophosphate may be one that is comprised of aluminum and phosphorus that are partly substituted by silicon, boron, Ni, Zn, Mg, Mn such as a porous crystalline metalaluminophosphate. The structure of such crystalline porous aluminophosphates may, for example, be those that are identified by codes for zeolites described above as AEL, AFI, AFO or FAU.

The above porous crystalline aluminophosphate is preferably a porous crystalline silicoaluminophosphate. Specifically, SAPOS, and the like having an AFI structure, SAPO41, and the like having an AFO structure, SAPO11, and the like having an AEL structure, structure or SAPO37, and the like having a FAU structure may be mentioned.

According to another specific embodiment, suitable catalysts for the present process is the silicoaluminophosphate molecular sieves, in particular of the AEL group with typical example the SAPO-11 molecular sieve. The SAPO-11 molecular sieve is based on the ALPO-11, having essentially an Al/P ratio of 1 atom/atom. During the synthesis silicon precursor is added and insertion of silicon in the ALPO framework results in an acid site at the surface of the micropores of the 10-membered ring sieve. The silicon content ranges from 0.1 to 10 atom % (where the sum of Al+P+Si is 100).

Various commercial zeolite products may be used, or it is possible to use zeolites that have been synthesized by a known method disclosed in the art.

According to a preferred embodiment the -cracking catalyst is a crystalline silicate containing advantageously at least one 10 members ring into the structure. It is by way of example of the MFI (ZSM-5, silicalite-1, boralite C, TS-1), MEL (ZSM-11, silicalite-2, boralite D, TS-2, SSZ-46), FER (Ferrierite, FU-9, ZSM-35), MTT (ZSM-23), MWW (MCM-22, PSH-3, ITQ-1, MCM-49), TON (ZSM-22, Theta-1, NU-10), EUO (ZSM-50, EU-1), MFS (ZSM-57), CON (CIT-1) and ZSM-48 family of microporous materials consisting of silicon, aluminium, oxygen and optionally boron. Advantageously the olefin cracking catalyst is a crystalline silicate, metal containing crystalline silicate or a dealuminated crystalline silicate.

The crystalline silicate can have a ratio Si/Al of at least about 100 and is advantageously selected among the MFI and the MEL. The crystalline silicate can advantageously be modified with the metals Mg, Ca, La, Ni, Ce, Zn, Co, Ag, Fe, Cu or Ga and mixtures thereof. In this latter case, the metal content is preferably at least 0.1 wt %.

The dealuminated crystalline silicate is advantageously such as about 10% by weight of the aluminium is removed. Such dealumination is advantageously made by a steaming optionally followed by a leaching.

In another preferred embodiment the crystalline silicate catalyst is mixed with a binder, preferably an inorganic binder, and shaped to a desired shape, e.g. pellets. The binder is selected so as to be resistant to the temperature and other conditions employed in the process of the disclosure. The binder is an inorganic material selected from clays, silica, metal silicate, metal borates, metal oxides such as $ZrO_2$ and/or metals, or gels including mixtures of silica and metal oxides.

According to a preferred embodiment the cracking catalyst is a P-modified zeolite (Phosphorus-modified zeolite). Said phosphorus modified molecular sieves can be prepared based on MFI, MOR, MEL, clinoptilolite or FER, MWW, TON, EUO, MFS and ZSM-48 family of microporous molecular sieves having an initial Si/Al ratio advantageously between 4 and 500. The P-modified zeolites of this recipe can be obtained based on cheap crystalline silicates with low Si/Al ratio (below 30).

By way of example said P-modified zeolite is made by a process comprising in that order:
  selecting a zeolite (advantageously with Si/Al ratio between 4 and 500) among $H^+$ or $NH_4^+$-form of MFI, MEL, FER, MOR, clinoptilolite, MWW, TON, EUO, MFS and ZSM-48;
  introducing P at conditions effective to introduce advantageously at least 0.05 wt % of P;
  separation of the solid from the liquid if any;
  an optional washing step or an optional drying step or an optional drying step followed by a washing step;
  a calcination step.

The zeolite with low Si/Al ratio has been made previously with or without direct addition of an organic template.

Optionally the process to make said P-modified zeolite comprises the steps of steaming and leaching. The method consists in steaming followed by leaching. It is generally known by the persons in the art that steam treatment of zeolites, results in aluminium that leaves the zeolite framework and resides as aluminium oxides in and outside the pores of the zeolite. This transformation is known as dealumination of zeolites and this term will be used throughout the text. The treatment of the steamed zeolite with an acid solution results in dissolution of the extra-framework aluminiumoxides. This transformation is known as leaching and this term will be used throughout the text. Then the zeolite is separated, advantageously by filtration, and optionally washed. A drying step can be envisaged between filtering and washing steps. The solution after the washing can be either separated, by way of example, by filtering from the solid or evaporated.

P can be introduced by any means or, by way of example, according to the recipe described in U.S. Pat. Nos. 3,911,041, 5,573,990 and 6,797,851.

The catalyst made of a P-modified zeolite can be the P-modified zeolite itself or it can be the P-modified zeolite formulated into a catalyst by combining with other materials that provide additional hardness or catalytic activity to the finished catalyst product. Advantageously, at least a part of phosphorous is introduced into zeolite before shaping. In a specific embodiment, the formed P-precursor can be further modified with the metals selected from Mg, Ca, La, Ni, Ce, Zn, Co, Ag, Fe, Cu according to the recipe described in WO 09092779 and WO 09092781.

The separation of the liquid from the solid is advantageously made by filtering at a temperature between 0-90° C., centrifugation at a temperature between 0-90° C., evaporation or equivalent.

Optionally, the zeolite can be dried after separation before washing. Advantageously said drying is made at a temperature between 40-600° C., advantageously for 1-10 h. This drying can be processed either in a static condition or in a gas flow. Air, nitrogen or any inert gases can be used.

The washing step can be performed either during the filtering (separation step) with a portion of cold (<40° C.) or hot water (>40 but <90° C.) or the solid can be subjected to a water solution (1 kg of solid/4 liters water solution) and treated under reflux conditions for 0.5-10 h followed by evaporation or filtering.

Final equilibration step is performed advantageously at the temperature 400-800° C. in presence of steam for 0.01-48h. Advantageously the steam partial pressure is at least 0.1 bars. Air, nitrogen or any inert gases can be fed together with steam.

According to a preferred embodiment the phosphorous modified zeolite is made by a process comprising in that order:
  selecting a zeolite (advantageously with Si/Al ratio between 4 and 500, from 4 to 30 in a specific embodiment) among $H^+$ or $N_4^+$-form of MFI, MEL, FER, MOR, clinoptilolite, MWW, TON, EUO, MFS and ZSM-48;
  steaming at a temperature ranging from 400 to 870° C. for 0.01-200 h;
  leaching with an aqueous acid solution at conditions effective to remove a substantial part of Al from the zeolite;
  introducing P with an aqueous solution containing the source of P at conditions effective to introduce advantageously at least 0.05 wt % of P;
  separation of the solid from the liquid;
  an optional washing step or an optional drying step or an optional drying step followed by a washing step;
  a calcination step.

Optionally between the steaming step and the leaching step there is an intermediate step such as, by way of example, contact with silica powder and drying.

Optionally the leaching and introducing P are made simultaneously by using an acid mixture comprising phosphorus to make the leaching.

Advantageously the selected MFI, MEL, FER, MOR, clinoptilolite, MWW, TON, EUO, MFS and ZSM-48 (or $H^+$ or $NH4^+$-form MFI, MEL, FER, MOR, clinoptilolite, MWW, TON, EUO, MFS and ZSM-48) has an initial atomic ratio Si/Al of 100 or lower and from 4 to 30 in a specific embodiment. The conversion to the $H^+$ or NR $4^+$-form is known per se and is described in U.S. Pat. Nos. 3,911,041 and 5,573,990.

Advantageously the final P-content is at least 0.05 wt % and preferably between 0.3 and 7 w %. Advantageously at least 10% of Al, in respect to parent zeolite MFI, MEL, FER, MOR and clinoptilolite, MWW, TON, EUO, MFS and ZSM-48, have been extracted and removed from the zeolite by the leaching.

Then the zeolite either is separated from the washing solution or is dried without separation from the washing solution. Said separation is advantageously made by filtration. Then the zeolite is calcined, by way of example, at 400° C. for 2-10 hours.

In the steam treatment step, the temperature is preferably from 420 to 870° C., more preferably from 480 to 760° C. The pressure is preferably atmospheric pressure and the water partial pressure may range from 13 to 100 kPa. The steam atmosphere preferably contains from 5 to 100 vol % steam with from 0 to 95 vol % of an inert gas, preferably nitrogen. The steam treatment is preferably carried out for a period of from 0.01 to 200 hours, advantageously from 0.05 to 200 hours, more preferably from 0.05 to 50 hours. The steam treatment tends to reduce the amount of tetrahedral aluminium in the crystalline silicate framework by forming alumina.

The leaching can be made with an organic acid such as citric acid, formic acid, oxalic acid, tartaric acid, malonic acid, succinic acid, glutaric acid, adipic acid, maleic acid, phthalic acid, isophthalic acid, fumaric acid, nitrilotriacetic acid, hydroxyethylenediaminetriacetic acid, ethylenediaminetetracetic acid, trichloroacetic acid trifluoroacetic acid or a salt of such an acid (e.g. the sodium salt) or a mixture of two or more of such acids or salts. The other inorganic acids may comprise an inorganic acid such as nitric acid, hydrochloric acid, methansulfuric acid, phosphoric acid, phosphonic acid, sulfuric acid or a salt of such an acid (e.g. the sodium or ammonium salts) or a mixture of two or more of such acids or salts.

The residual P-content is adjusted by P-concentration in the aqueous acid solution containing the source of P, drying conditions and a washing procedure if any. A drying step can be envisaged between filtering and washing steps.

Said P-modified zeolite can be used as itself as a catalyst. In another embodiment it can be formulated into a catalyst by combining with other materials that provide additional hardness or catalytic activity to the finished catalyst product. Materials which can be blended with the P-modified zeolite can be various inert or catalytically active materials, or various binder materials. These materials include compositions such as kaolin and other clays, various forms of rare earth metals, phosphates, alumina or alumina sol, titania, zirconia, quartz, silica or silica sol, and mixtures thereof. These components are effective in densifying the catalyst and increasing the strength of the formulated catalyst. The catalyst may be formulated into pellets, spheres, extruded into other shapes, or formed into a spray-dried particles. The amount of P-modified zeolite which is contained in the final catalyst product ranges from 10 to weight percent of the total catalyst, preferably 20 to 70 weight percent of the total catalyst.

Final equilibration step is performed advantageously at the temperature 400-800° C. in presence of steam for 0.01-48h. Advantageously the steam partial pressure is at least 0.1 bars. Air, nitrogen or any inert gases can be fed together with steam.

A possible catalyst for the olefin cracking is described in WO2009098262.

With regards to the operating conditions of step d), the cracking reaction can be performed in a fixed bed reactor, a moving bed reactor or a fluidized bed reactor. A typical moving bed reactor is of the continuous catalytic reforming type. The process may also be performed continuously using a pair of parallel swing reactors.

The operating conditions of step d) are selected to disfavor hydrogen transfer reactions leading to the formation of paraffins, aromatics and coke precursors. The operating conditions thus employ a high space velocity, a low pressure and a high reaction temperature. Preferably, the LHSV ranges from 1 to 30 $h^{-1}$, preferably from 5 to 20 $h^{-1}$, more preferably from 5 to 15 $h^{-1}$. The hydrocarbon feedstocks are preferably fed at a total inlet pressure sufficient to convey the feedstocks through the reactor. Preferably, the total pressure in the reactor ranges from 0.5 to barg, preferably from 0.5 to 5 barg, more preferably from 0.5 to 2 barg. The use of a low olefin partial pressure, for example atmospheric pressure, tends to lower the incidence of hydrogen transfer reactions in the cracking process, which in turn reduces the potential for coke formation which tends to reduce catalyst stability. The cracking of the olefins and/or long chain paraffins is preferably performed at an inlet temperature of the feedstock of from 500 to 650° C., more preferably from 520 to 600° C., yet more preferably from 540 to 580° C., typically around 560° C. to 580° C. In accordance with a preferred aspect of the present disclosure, the hydrogen gas can be introduced into the olefin-containing feedstock preferably at a hydrogen partial pressure between 1 and 7.5 barg. Typically, the addition of hydrogen to the feedstock permits increasing the cycle time between successive regenerations of the catalyst. The inventive process is however advantaging in that the H2 consumption stays very low if not null. With regards to step e), the separation from the effluents of step d) is carried out by any means, they are known per se. None limiting examples of separation include distillation and flash.

With regards to the purification of the first stream in step e), it can be preferably performed with a caustic scrubber. A scrubber unit containing a caustic solution (e.g. a solution of sodium hydroxide in water) can be used. It allows removing (e.g. via reaction, adsorption, absorption or combination thereof) sulfur and chlorine containing gases from the gaseous stream to yield the treated gas stream which can further integrate the downstream purification section of the steam cracker. This purification step allows to integrate gas stream obtained in an existing steam cracker plant.

With regards to the waste plastic pyrolysis, an example of a pyrolysis process for waste plastics is disclosed in U.S. Pat. No. 8,895,790 or in US2014/0228606 and in WO 2016/009333.

In a waste plastic pyrolyzer, mixed plastics (e.g., waste plastics) are placed in pyrolysis unit or pyrolyzer. In the pyrolysis unit, the waste plastic is converted via pyrolysis to a pyrolysis product, wherein the pyrolysis product comprises a gas phase (e.g., pyrolysis gases, such as C1 to C4 gases, hydrogen (H2), carbon monoxide (CO), carbon dioxide (CO2) mainly) and a liquid phase being pyrolysis plastic oil. The plastic waste may include post-consumer waste plastics, such as mixed plastic waste. Mixed plastics can comprise non-chlorinated plastics (e.g., polyolefins, polyethylene, polypropylene, polystyrene, copolymers, etc.), chlorinated plastics (e.g., polyvinylchloride (PVC), polyvinylidene chloride (PVDC), etc.), and the like, or mixtures thereof. Generally, waste plastics comprise long chain molecules or polymer hydrocarbons. Waste plastics may also include used tires.

The pyrolysis unit may be any suitable vessel configured to convert waste plastics into gas phase and liquid phase products (e.g., simultaneously). The vessel may be configured for gas phase, liquid phase, vapor-liquid phase, gas-solid phase, liquid-solid phase, or slurry phase operation. The vessel may contain one or more beds of inert material or pyrolysis catalyst comprising sand, zeolite, alumina, a catalytic cracking catalyst, or combinations thereof. Generally, the pyrolysis catalyst is capable of transferring heat to the components subjected to the pyrolysis process in the pyrolysis unit. Alternatively, the pyrolysis unit can be operated without any catalyst (e.g., pure thermal pyrolysis). The pyrolysis unit may be operated adiabatically, isothermally, nonadiabatically, non-isothermally, or combinations thereof. The pyrolysis reactions of this disclosure may be carried out in a single stage or in multiple stages. For example, the pyrolysis unit can be two reactor vessels fluidly connected in series.

In a configuration where the pyrolysis unit comprises two vessels, the pyrolysis process may be divided into a first stage which is performed in a first vessel and in a second stage fluidly connected downstream of the first stage which is performed in the second vessel. As will be appreciated by one of skill in the art, and with the help of this disclosure, the second stage may enhance the pyrolysis of an intermediate pyrolysis product stream flowing from the first stage into the second stage, to yield a pyrolysis product flowing from the second stage. In some configurations, the first stage may utilize thermal cracking of the waste plastics, and the second stage may utilize thermal or catalytic cracking of the waste plastics to yield the pyrolysis product flowing from the second stage. Alternatively, the first stage may utilize catalytic cracking of the waste plastics, and the second stage may utilize thermal or catalytic cracking of the waste plastics to yield the pyrolysis product flowing from the second stage.

In some configurations, the pyrolysis unit may include one or more equipment configured to convert mixed plastics into gas phase and liquid phase products. The one or more equipment may or may not contain an inert material or pyrolysis catalyst as described above. Examples of such equipment include one or more of heated extruders, heated rotating kiln, heated tank-type reactors, packed bed reactors, bubbling fluidized bed reactors, circulating fluidized bed reactors, empty heated vessels, enclosed heated surfaces where plastic flows down along the wall and cracks, vessels surrounded by ovens or furnaces, or any other suitable equipment offering a heated surface to assist in cracking.

The pyrolysis unit can be configured to pyrolyze (e.g., crack), and in some aspect (e.g., where hydrogen is added to the pyrolysis unit), additionally hydrogenate components of the waste plastic stream fed to the pyrolysis unit. Examples of reactions which may occur in the pyrolysis unit include, but are not limited to isomerization of one or more normal paraffins to one or more i-paraffins, selective ring opening of one or more cycloparaffins to one or more i-paraffins, cracking of long chain length molecules to short chain length molecules, removal of heteroatoms from heteroatom-containing hydrocarbons (e.g., dechlorination), hydrogenation of coke generated in the process, or combinations thereof.

In one or more configurations of the pyrolysis unit, a head space purge gas can be utilized in all or a portion of the pyrolysis stage(s) (conversion of waste plastics to a liquid phase and/or gas phase products) to enhance cracking of plastics, produce valuable products, provide a feed for steam cracking, or combinations thereof. The head space purge gas may include hydrogen (H2), C1 to C4 hydrocarbon gases (e.g., alkanes, methane, ethane, propane, butane, isobutane), inert gases (e.g., nitrogen (N2), argon, helium, steam), and the like, or combinations thereof. The use of a head space purge gas assists in the dechlorination in the pyrolysis unit, when the waste plastic comprises chlorinated plastics. The head space purge gas may be introduced to the pyrolysis unit to aid in the removal of volatiles entrained in the melted mixed plastics present in the pyrolysis unit.

A hydrogen (H2) containing stream can be added to the pyrolysis unit to enrich the pyrolysis unit environment with H2, assist in stripping entrapped hydrogen chloride in the pyrolysis unit, provide a local environment rich in hydrogen in the pyrolysis melt or liquid, or combinations thereof; for example via a H2 containing stream fed directly to the pyrolysis unit independently of the waste plastic stream. In some aspects, H2 can also be introduced along with stream to the pyrolysis unit, with adequate safety measures incorporated for hydrogen handling with plastics feed.

The pyrolysis unit may facilitate any reaction of the components of the waste plastic stream in the presence of, or with, hydrogen. Reactions may occur such as the addition of hydrogen atoms to double bonds of unsaturated molecules (e.g., olefins), resulting in saturated molecules (e.g., paraffins, i-paraffins, naphthenes). Additionally or alternatively, reactions in the pyrolysis unit may cause a rupture of a bond of an organic compound, with a subsequent reaction and/or replacement of a heteroatom with hydrogen.

The use of hydrogen in the pyrolysis unit can have beneficial effects of i) reducing the coke as a result of cracking, ii) keeping the catalyst used (if any) in the process in an active condition, iii) improving removal of chloride from stream such that the pyrolysis product from pyrolysis unit is substantially dechlorinated with respect to waste plastic stream, which minimizes the chloride removal requirement in units downstream of the pyrolysis unit, iv) hydrogenating of olefins, v) reducing diolefins in pyrolysis product, vi) helping operate the pyrolysis unit at reduced temperatures for same levels of conversion of waste plastic stream in the pyrolysis unit, or combinations of i)-vi).

The pyrolysis processes in the pyrolysis unit may be low severity or high severity. Low severity pyrolysis processes may occur at a temperature of less than about 450° C., alternatively 250° C. to 450° C., alternatively 275° C. to 425° C., or alternatively 300° C. to 400° C., and may produce pyrolysis oils rich in mono- and di-olefins as well as a significant amount of aromatics. High severity pyrolysis processes may occur at a temperature of equal to or greater than about 450° C., alternatively 450° C. to 750° C., alternatively 500° C. to 700° C., or alternatively 550° C. to 650° C., and may produce pyrolysis oils rich in aromatics, as well as more gas products (as compared with low severity pyrolysis). As will be appreciated by one of skill in the art, a high severity pyrolysis process will lead to the formation of more olefins and diolefins. Those olefins and diolefins cannot easily be recovered. The hydrotreatment of the present disclosure is therefore required.

A pyrolysis product can be recovered as an effluent from the pyrolysis unit and conveyed (e.g., flowed, for example via pumping, gravity, pressure differential, etc.) to a pyrolysis separating unit. The pyrolysis product can be separated in the pyrolysis separating unit into a pyrolysis gas stream and a pyrolysis plastic oil further used in step a) of the present disclosure. The pyrolysis separating unit may comprise any suitable gas-liquid separator, such as a vapor-liquid separator, oil-gas separators, gas-liquid separators, degassers, deliqulizers, scrubbers, traps, flash drums, compressor suction drums, gravity separators, centrifugal separators, filter vane separators, mist eliminator pads, liquid-gas coalescers, distillation columns, and the like, or combinations thereof.

With regards to the steam cracker, it is known per se in the art. The feedstock of the steam cracker in addition to the stream obtained via the inventive process can be ethane, liquefied petroleum gas, naphtha or gasoils. Liquefied petroleum gas (LPG) consists essentially of propane and butanes. Gasoils have a boiling range from about 200 to 350° C., consisting of C10 to C22 hydrocarbons, including essentially linear and branched paraffins, cyclic paraffins and aromatics (including mono-, naphtho- and poly-aromatic).

In particular, the cracking products obtained at the exit of the steam cracker may include ethylene, propylene and benzene, and optionally hydrogen, toluene, xylenes, and 1,3-butadiene.

In a preferred embodiment, the outlet temperature of the steam cracker may range from 800 to 1200° C., preferably from 820 to 1100° C., more preferably from 830 to 950° C., more preferably from 840° C. to 920° C. The outlet temperature may influence the content of high value chemicals in the cracking products produced by the present process.

In a preferred embodiment, the residence time in the steam cracker, through the radiation section of the reactor where the temperature is between 650 and 1200° C., may range from 0.005 to 0.5 seconds, preferably from 0.01 to 0.4 seconds.

In a preferred embodiment, steam cracking is done in presence of steam in a ratio of 0.1 to 1.0 kg steam per kg of hydrocarbon feedstock, preferably from 0.25 to 0.7 kg steam per kg of hydrocarbon feedstock in the steam cracker, preferably in a ratio of 0.35 kg steam per kg of feedstock mixture, to obtain cracking products as defined above.

In a preferred embodiment, the reactor outlet pressure may range from 500 to 1500 mbars, preferably from 700 to 1000 mbars, more preferably may be approx. 850 mbars. The residence time of the feed in the reactor and the temperature are to be considered together. A lower operating pressure results in easier light olefins formation and reduced coke formation. The lowest pressure possible is accomplished by (i) maintaining the output pressure of the reactor as close as possible to atmospheric pressure at the suction of the cracked gas compressor (ii) reducing the pressure of the hydrocarbons by dilution with steam (which has a substantial influence on slowing down coke formation). The steam/feedstock ratio may be maintained at a level sufficient to limit coke formation.

Effluent from the steam cracker contains unreacted feedstock, desired olefins (mainly ethylene and propylene), hydrogen, methane, a mixture of C4's (primarily isobutylene and butadiene), pyrolysis gasoline (aromatics in the C6 to C8 range), ethane, propane, di-olefins (acetylene, methyl acetylene, propadiene), and heavier hydrocarbons that boil in the temperature range of fuel oil (pyrolysis fuel oil). This cracked gas is rapidly quenched to 338-510° C. to stop the pyrolysis reactions, minimize consecutive reactions and to recover the sensible heat in the gas by generating high-pressure steam in parallel transfer-line heat exchangers (TLE's). In gaseous feedstock-based plants, the TLE-quenched gas stream flows forward to a direct water quench tower, where the gas is cooled further with recirculating cold water. In liquid feedstock-based plants, a prefractionator precedes the water quench tower to condense and separate the fuel oil fraction from the cracked gas. In both types of plants, the major portions of the dilution steam and heavy gasoline in the cracked gas are condensed in the water quench tower at 35-40° C. The water-quench gas is subsequently compressed to about 25-35 Bars in 4 or 5 stages. Between compression stages, the condensed water and light gasoline are removed, and the cracked gas is washed with a caustic solution or with a regenerative amine solution, followed by a caustic solution, to remove acid gases (CO2, H2S and SO2). The compressed cracked gas is dried with a desiccant and cooled with propylene and ethylene refrigerants to cryogenic temperatures for the subsequent product fractionation: front-end demethanization, front-end depropanization or front-end deethanization.

The disclosure can be further defined using the following embodiments:

Embodiment 1. Process to produce olefins from a hydrocarbon stream comprising pyrolysis plastic oil comprising the following steps:
- a) Providing a hydrocarbon stream containing at least 10 wt % of pyrolysis plastic oil preferably 25 wt %, even more preferably 50 wt %, even more preferably 75 wt % the other part of said hydrocarbon stream being a first diluent;
- b) Optionally putting in contact the effluent obtained at the previous step with a silicon and/or metals and/or phosphorous and/or halogenates trap, and/or water trap;
- c) optionally performing a selective hydrogenation step at a temperature of at most 200° C. so that the effluents obtained at the exit of said selective hydrogenation step has a diene value of at most 3 gI2/100 g, preferably at most 2.0 gI2/100 g even more preferably at most 0.5 gI2/100 g as measured according to UOP 326;
- d) contacting the stream obtained at the previous step, being preferably diluted with a second diluent, with a cracking catalyst being a 10 MR and/or 12 MR molecular sieve at a temperature ranging from 450° C. to 650° C. and a total pressure ranging from 0.5 to 10 barg to crack the olefins and/or paraffins of said pyrolysis plastic oil into olefins having 2 to 4 carbon atoms;
- e) separating from the effluents obtained at the previous step a first stream containing olefins and saturated hydrocarbons having at most 3 carbon atoms, and a second stream containing hydrocarbons having 4 or more carbon atoms;
- f) recovering from said first stream the ethylene and propylene.

Embodiment 2. Process according to previous embodiment wherein said pyrolysis plastic oil in said hydrocarbon stream has a starting boiling point of at least 15° C., and a final boiling point of preferably 560° C., more preferably 450° C. even more preferably 350° C., the most preferred 250° C.

Embodiment 3. Process according to any of the previous embodiments wherein said pyrolysis plastic oil has a diene value of at least 1.5, preferably 2, even more preferably 5 gI2/100 g, to at most 50 gI2/100 g as measured according to UOP 326, and/or contains more than 2 ppm wt of metals.

Embodiment 4. Process according to any of the previous embodiments wherein said hydrocarbon stream contains at least 25 wt %, preferably at least 50 wt %, even more preferably at least 75 wt % of said pyrolysis plastic oil and preferably at most 80 wt % of pyrolysis plastic oil, and/or at most 90 wt % preferably at most 95 wt %, even more preferably at most 100 wt % of said pyrolysis plastic oil.

Embodiment 5. Process according to any of the preceding embodiments wherein said first diluent is selected from an olefinic or paraffinic refinery or petrochemical stream including butenes, pyrolysis gasoline from a steam cracker, light cracked naphtha spirit from a FCC, coker naphtha from a coker, or a saturated hydrocarbon, having a boiling range from 15 to 250° C., preferably 75 to 200° C., as measured with method ASTM D2887, preferably said first diluent is part of said second stream recovered at step e) or any combination thereof.

Embodiment 6. Process according to any of the preceding embodiments wherein the weight concentration of said pyrolysis plastic oil in said hydrocarbon stream at the inlet of the catalytic cracking step d) is chosen so that the total content of olefins in said hydrocarbon stream is at most 60 wt %, preferably at most 55 wt %, most preferably at most 50 wt %.

Embodiment 7. Process according to any of the preceding embodiments wherein concerning said selective hydrogenation step of said hydrocarbon stream, one or more of the following statements is true:
- The inlet temperature ranges from 25 to 200° C.;
- The LHSV ranges from 1 to 10 h−1, preferably from 1 to 6 h−1, even more preferably from 2 to 4 h−1;
- The pressure ranges from 5 to 90 barg, preferably from 15-50 barg or preferably from 25 to 40 barg in presence of H2, and/or the molar ratio of H2 to the total molar sum of alkynes and dienes in said hydrocarbon stream is of at least 1.5, preferably at least 2, most preferably at least 3 to at most 15;
- Said selective hydrogenation step is performed in one or more catalyst bed with preferably an overall temperature increase of at most 150° C., more preferably of at most 100° C., and/or a temperature increase of at most 100° C., more preferably of at most 50° C. for each catalyst bed, with preferably intermediary quench between said catalyst beds, said quench being preferably performed with H2 or with the effluents of said selective hydrogenation step;
- said first step is performed in a fixed bed reactor preferably over a catalyst that comprises at least one metal of group VIII, preferably selected from the group of Pt, Pd, Ni and/or mixture thereof on a support such as alumina, titania, silica, zirconia, magnesia, carbon; preferably said catalyst is a Ni based catalyst being a passivated after its reduction using preferably di-alkyl-sulfide such as DiMethylSulfide (DMS) or DiEthylSulfide (DES) or thiophenic compounds;
- said first step can also be performed in a fixed bed reactor preferably over a catalyst that comprises at least one metal of group VIB as for example Mo, W in combination with or not with a promotor selected from at least one metal of group VIII and/VIIIB as for example Ni and/or Co, and/or mixture thereof, these metals being used in sulfided form and preferably supported on alumina, titania, zirconia, silica, carbon and/or mixtures thereof; and/or
- the effluents obtained at the exit of said selective hydrogenation step has a diene value of at most 1.5 gI2/100 g, preferably at most 1.0 gI2/100 g even more preferably at most 0.5 gI2/100 g.

Embodiment 8. Process according to any of the preceding embodiments wherein for said step d) of contacting the stream obtained at the previous step with a cracking catalyst one or more of the following statements is true:
- temperature of cracking reaction ranges from 500 to 650° C., more preferably from 520 to 600° C., yet more preferably from 540 to 580° C., typically around 560° C. to 580° C.;
- the cracking reaction is performed in a fixed bed reactor, or a moving bed reactor or a fluidized bed reactor;
- the LHSV ranges from 1 to 30 h−1, preferably from 5 to 20 h−1, more preferably from 5 to 15 h−1;
- The total pressure in the reactor ranges from 0.5 to 10 barg, preferably from 0.5 to 5 barg, more preferably from 0.5 to 2 barg;
- The cracking reaction is performed without hydrogen or hydrogen is present at pressure from 0.5 to 7.5 barg preferably at a pressure of maximum 2.5 barg, more preferably at a pressure of maximum 1.5 barg; and/or
- The catalyst is selected from SAPO-5, and the like having an AFI structure, SAPO-41, and the like having an AFO structure, SAPO-11, and the like having an AEL structure, structure or SAPO-37, and the like having a FAU structure with preferably a silicon content ranging from 1.0 to 10 atom %, where the sum of Al+P+Si is 100, or MFI, for instance ZSM-5, silicalite-1, boralite C, TS-1; MEL, for instance ZSM-11, silicalite-2, boralite D, TS-2, SSZ-46; FER for instance Ferrierite, FU-9, ZSM-35; MTT for instance ZSM-23; MWW for instance MCM-22, PSH-3, ITQ-1, MCM-49; TON for instance ZSM-22, Theta-1, NU-10; EUO for instance ZSM-EU-1; MFS for instance ZSM-57; CON like CIT-1; and ZSM-48 family of microporous materials consisting of silicon, aluminium, oxygen and optionally boron; preferably the cracking catalyst is a crystalline silicate, metal containing crystalline silicate or a dealuminated crystalline silicate or any mixture thereof; most preferably the cracking catalyst has a MFI or the MEL structure advantageously modified with the metals Mg, Ca, La, Ni, Ce, Zn, Co, Ag, Fe, Cu or Ga or mixtures thereof with a metal content preferably of at least 0.1 wt % and at most wt %; preferably the cracking catalyst is a P-modified zeolite, Phosphorus-modified zeolite, preferably prepared based on MFI, MOR, MEL, clinoptilolite or FER, MWW, TON, EUO, MFS and ZSM-48 family having an initial Si/Al ratio advantageously between 4 and 500.

Embodiment 9. Process according to any of the preceding embodiments wherein said trap of step b) is a silicon trap working at a temperature ranging from 20 to 200° C. and/or a LHSV between 1 to 10 h−1, and/or a pressure ranging from 1 to 90 barg and/or said trap of step b) is followed by a metal trap working at a temperature of at most 200° C., and/or a LHSV between 1 to 10 h−1, and/or a pressure ranging from 1 to 90 barg in presence of H2.

Embodiment 10. The process according to any of the preceding embodiments wherein said pyrolysis plastic oil and/or said hydrocarbon stream of step a) is treated before step b) in one or more of the followed pre-treatment unit:
In a desalting unit to remove water-soluble salts;
In an impurities removal treatment step to remove silicon, phosphorous, metals and/or halogenated compounds, via preferably a solvent extraction or preferably in a guard bed, said guard bed preferably working at a temperature of at most 200° C., and/or a LHSV between 1 to 10 h−1, and/or a pressure ranging from 1 to 90 barg either in presence of H2 or in the absence of H2 and/or said guard bed is followed by a metal trap working at a temperature of at least 200° C., and/or a LHSV between 1 to 10 h−1, and/or a pressure ranging from 1 to 90 barg in presence of H2;
In a separation unit to extract the particles and gums by filtration, centrifugation or a combination of the two technics; and/or
In a dewatering unit to remove water in said hydrocarbon stream to reach a water content of less than 0.1% vol preferably of less than 0.05% vol according to ASTM D95.

Embodiment 11. The process according to any of the preceding embodiments wherein after step e) hydrocarbons having 4 to 6 carbon atoms are separated from said second stream to be further cracked preferably by recycling them at step d).

Embodiment 12. The process according to any of the preceding embodiments wherein the hydrocarbons having at least 7 carbon atoms are separated from said second stream, hydrogenated and/or hydrotreated and sent to a steam cracker to be cracked into olefins.

Embodiment 13. The process according to any of the preceding embodiments wherein said pyrolysis plastic oil of step a) is originating from the stream of pyrolyzed waste plastic for which the C1 to C4 hydrocarbons have been removed and/or the components having a boiling point higher than 350° C. have been removed and/or preferably further converted into a FCC, or an hydrocracking unit, a coker or a visbreaker or blended in crude oil or crude oil cut to be further refined.

Embodiment 14. The process according to any of the preceding embodiments wherein the hydrocarbons having a boiling point higher than 350° C. are removed from said second stream and are further converted into a FCC, or an hydrocracking unit, a coker or a visbreaker or blended in crude oil or crude oil cut to be further refined.

Embodiment 15. The process according to any of the preceding embodiments wherein said first diluent is selected from an olefinic refinery or petrochemical stream including butenes, pyrolysis gasoline from a steam cracker, light cracked naphtha spirit from a FCC, coker naphtha from a coker, or a saturated hydrocarbon, having a boiling range from 15 to 250° C., preferably 75 to 200° C., as measured with method ASTM D2887, preferably said first diluent is part of said second stream recovered at step e) or any combination thereof.

Embodiment 16. The process according to any of the preceding embodiments wherein said second diluent is incorporated at step d) so that the olefins content at the inlet step d) is at most 60 wt %, preferably at most 55 wt %, most preferably at most 50 wt %, being and olefinic or paraffinic refinery stream, even more preferably said second diluent is a naphtha having a boiling range from 15 to 250° C., preferably 38 to 150° C., as measured with method ASTM D2887 or a saturated hydrocarbon solvent, having a boiling range from 15 to 250° C., preferably 75 to 200° C., as measured with method ASTM D2887, or a part of said second stream recovered at step e), or preferably being N-pentane or iso-paraffinic solvent, or any mixture thereof.

EXAMPLES

The embodiments of the present disclosure will be better understood by looking at the different examples below.

A typical detailed composition of a pyrolyzed plastic oil used is to find in Table 1.

| | | | |
|---|---|---|---|
| Density at 15° C. | kg/m$^3$ | NF EN ISO 12185 | 800.2 |
| | | ASTM D4052 | |
| TAN | mgKOH/g | | 5.1 |
| Composition | | | |
| Olefin content (NMR) | % wt | | 69 |
| Bromine number | g Br/100 g | ASTM D1159 | 81 |
| Diene value | g I$_2$/100 g | | 2 |
| MAV | mg of maleic anhydre/ 1 g | ASTM UOP326-17 | 7.8 |
| Gums Jets | mg/100 ml | IP 540 | |
| N | ppm | ASTM D4629 | 210 |
| S | ppm | ISO 20846 | 18.6 |
| Distillation ISO | | | TBP |
| T0 | ° C. | NF EN ISO 3405 | 69 |
| T 5% | ° C. | ISO 20846 | 125 |
| T 50% | ° C. | | 214 |
| T 95% | ° C. | NF EN ISO 3405 | 381 |
| FBP | ° C. | NF EN ISO 3405 | 461 |
| Metals | | | |
| Al | ppm | | <1 |
| As | ppm | | <1 |
| Ca | ppm | | <1 |
| Ce | ppm | | <8 |

| | | |
|---|---|---|
| K | ppm | <8 |
| Na | ppm | 11.7 |
| P | ppm | 3.3 |
| Si | ppm | 198 |
| Total metals | ppm | |
| Cl total | ppm | 109 |
| Water content | % | 0.055 |
| Ionic Compounds | | |
| Acetate | ppm | 450 |
| Propioniate | ppm | 165 |
| Formiate | ppm | 21 |
| Nitrate | ppm | nd |
| Sulfate | ppm | 1030 |
| Fluorides | ppm | 4.9 |
| Chlorides | ppm | 2.5 |
| Nitrites | ppm | 11.7 |
| Bromides | ppm | 7.3 |

Example 1: Catalytic Cracking Step Applied to Pyrolyzed Plastic Oil

The catalyst is a shaped cylinder catalyst containing 30% wt of binder (silica) and 70% wt of silicalite (MFI), which has been steamed and acid exchanged, leading to an overall Si/Al of around 250.

The catalyst was loaded in a fixed bed reactor of 11 mm diameter. The formulated catalyst was crushed and the particles of 35 to 45 mesh size retained for the test. Before the reaction, the catalyst is activated under nitrogen at 575° C. for 6 hours (heating rate 60° C./h).

The reactor was operated at a pressure of 1.3 bara at the outlet. Hydrogen is fed into the reactor at a flowrate of 1-2 NL/h.

The reactor was fed with the ex-plastic pyrolysis oil described in table 1 diluted with 75% wt pentane. The overall LHSV (liquid Hour Space Velocity) was 10 $h^{-1}$. The reactor inlet temperature was 575° C.

The analysis of the gaseous effluent was performed using on-line micro-GC.

The liquid fraction was recovered and further analyzed.

| Table 2 provides the catalyst performance Feed | Pyrolyzed plastic oil |
|---|---|
| P (bara) | 1.5 |
| T(° C.) | 575 |
| WHSV (h-1) | 10 |

At the outlet of the reactor, after 24 hours time of stream, 60% wt of the ex-plastic oil is converted into a gaseous stream having the following composition, after substraction of the diluent (n-pentane) contribution:

| Compounds | % wt |
|---|---|
| methane | 5.8 |
| ethylene | 13.7 |
| ethane | 10.8 |
| propylene | 44.4 |
| propane | 2.9 |
| propadiene | 0.01 |
| cyclopropane | 0.008 |
| Paraffin C4 | 0.6 |
| Olefins C4 | 17.8 |
| 1,3-butadiene | 0.3 |
| Olefins 5 | 3.5 |

The propylene over ethylene molar ratio is of 2.32, corresponding to a weight ratio of 3.2.

The propylene purity is of 93.7% wt. The simulated distillation of the remaining liquid product (after substraction of the n-C5 contribution) is presented on the FIG. 2. The T95% wt of the pyrolysis oil is 233° C., proving that most of the pyrolysis oil has been successfully converted into light olefins (C2-+C3-).

Example 2: Liquid Phase First Stage Hydrotreatment

The tests were performed using a pyrolysis plastic oil cut having a boiling point ranging from 70° C. to 460° C., a DV of about 4 gI2/100 g, a nitrogen content of about 210 wtppm and a sulfur content of about 20 ppm. A Ni on alumina catalyst was used in dilution 1:2 with silicon carbide 0.21 mm as diluent (50 ml of catalyst for 100 ml of SiC). The Nickel catalyst was dried under nitrogen (50 Nl/h) at 180° C. and reduced under hydrogen (minimum 20 Nl/h) at about 400° C. during min 15h; then the temperature was reduced till 180° C. and the hydrogen was replaced by nitrogen to purge the reactor. Finally, the temperature was reduced to 50° C. and a paraffinic feed was injected to stabilize the catalyst. The pyrolysis plastic oil cut was used pure. The test was performed in the following operating conditions.

| | |
|---|---|
| Pression (barg) | 30 |
| LHSV ($h^{-1}$) | 2 |
| Q liquid (ml/h) | 100 |
| Q_H2 (Nl/h) | 3 moles of hydrogen per mole of dienes. |
| Temperature (° C.) | Start Of Run: 50° |

The temperature was increased till having the lowest DV in the liquid effluent. The Bromine number (BrN) is mentioned for information and to highlight that not all the olefins have been hydrogenated in these conditions.

| Tinlet (° C.) | Feed DV (gI2/100 g) | Effluent DV (gI2/100 g) | Feed BrN (gBr2/100 g) | Effluent BrN (gBr2/100 g) |
|---|---|---|---|---|
| 50 | 4.1 | 1.9 | 60.1 | 46.3 |
| 60 | 4.1 | 1.8 | 60.1 | 54.9 |
| 90 | 4.1 | 0.1 | 60.1 | 47.2 |

No noticeable exotherm was observed during the test, whatever the inlet Temperature considered. Increasing the temperature up to 120° C., allowed to decrease the Bromine number down to 42 gBr2/g. This example demonstrates that it is possible to hydrogenate the diolefins and the olefins of a pyrolysis plastic oil while maintaining the exothermicity in the catalyst bed at an acceptable level.

Example 3

Liquid Phase First Stage Hydrotreatment

The tests were performed using a pyrolysis oil cut having a boiling point ranging from 20 to 250° C., a MAV of about 32. A sulfided NiMo on alumina catalyst was used in dilution with silicon carbide at equal volumes.

The catalyst was dried under nitrogen (50 Nl/h) at 180° C. and stabilized under a paraffinic feed at 50° C.

The pyrolysis oil cut was diluted with a paraffinic diluent to have a MAV at the inlet of about 21 mg anhydride maleic/g (or a DV of about 5.4 gI2/100 g).

The test was performed in the following operating conditions.

| | |
|---|---|
| Pression (barg) | 25 |
| LHSV (h$^{-1}$) | 2 |
| liquide flow rate (ml/h) | 200 |
| H$_2$/HC (Nl/l) | 7 |
| H2 flow rate (Nl/h) | 1.4 |
| Inlet Temperature (° C.) | Start Of Run: 50° |

No noticeable exotherm was observed during the test, whatever the inlet Temperature considered. The temperature was increased till having a MAV under 5.4 mg anhydride maleic/g (or a DV under 1.3 gI2/100 g) in the liquid effluent. This example demonstrates that it is possible to hydrogenate the diolefins and the olefins of a pyrolysis plastic oil while maintaining the exothermicity in the catalyst bed at an acceptable level.

Example 5: Adsorbents Used in Fixed Bed Reactor

It is foreseen that adsorbents will behave as it is presented in the results below. The tests were performed using a pyrolysis plastic oil cut having a boiling point ranging from 40° C. to 350° C. The water is expected to be below 100 ppm weight. The chlorine content of is expected to be in the range of about 200 ppm, the silicon content is expected to be in the range of about 100 ppm. The oxygen content of is expected in the range of about 1.0 wt %. The nitrogen is probably less than 2000 ppm wt. The adsorbent is chosen as being a promoted alumina (or active aluminium oxide) of spherical shape with 3.0 mm mean diameter with a surface area of 220 m2/g and a density of 0.75 kg/L. The adsorbent is disposed in a fixed bed under a continuous flow. Before the test the adsorbent shall be dried under nitrogen in up flow mode. The pyrolysis plastic oil shall be injected up flow. Dilution of the pyrolysis plastic oil with a first diluent can be done prior to the adsorption over the adsorbent. Alternatively, the pyrolysis plastic oil can be passed through the adsorbent without being diluted. This latter option was estimated in this example. The pyrolysis oil was injected in up flow mode at 20° C. under nitrogen blanketing.

| | | Pyrolysis Oil |
|---|---|---|
| Density @15° C. | g/mL | 0.80 |
| Silicon | ppm | 100 |
| Oxygen | wt % | 1.0 |
| Chlorine | ppm | 200 |
| Nitrogen | ppm | 2000 |

The tests were performed at ambient temperature (20° C.) and at three LHSV. The different operating conditions and performances expected are summarized in the following table, wherein weight percentage is given as the removed proportion of each measured element after treatment relative to the proportion of said element in the feedstock (here: plastic pyrolysis oil) before treatment. For sake of clarity, "100 wt %" means that the entirety of the component of interest has been removed:

| Condition | Pressure (barg) | LHSV (h$^{-1}$) | T (° C.) | Oxygen wt % | Chlorine wt % | Silicon wt % | Nitrogen wt % |
|---|---|---|---|---|---|---|---|
| 1 | 1 | 0.5 | 20 | 30 | 15 | 5 | 18 |
| 2 | 1 | 1 | 20 | 28 | 12 | 2 | 12 |
| 3 | 1 | 2 | 20 | 23 | 10 | n.s. | 9 |

*n.s. = not significant;

Impurities measurement was done at start of run. The overall oxygen uptake by the adsorbent is ranging from 2 to 15 wt % depending on operating conditions especially LHSV and the physical-chemical properties and nature of adsorbent used. This overall uptake corresponds to the maximal amount of oxygen containing impurities which can be trapped within the said adsorbent.

Very similar results can be obtained with silica gel having a spherical diameter of 5 mm, a surface area of about 500 m2/g, a density of 600 kg/m3 and a pore volume of about 0.42 cm3/g. The expected results with the same operating conditions are presented below

| Condition | Pressure (barg) | LHSV (h$^{-1}$) | T (° C.) | Oxygen wt % | Chlorine wt % | Silicon wt % | Nitrogen wt % |
|---|---|---|---|---|---|---|---|
| 1 | 1 | 0.5 | 20 | 20 | 12 | 7 | 30 |
| 2 | 1 | 1 | 20 | 15 | 9 | 5 | 22 |
| 3 | 1 | 2 | 20 | 11 | 7 | n.s. | 416 |

*n.s. = not significant;

It appears from the examples described above that the promoted alumina and silica gel should allow to trap oxygen, chlorine, nitrogen and also silicon to a certain extend too.

The invention claimed is:

1. Process to produce olefins from a hydrocarbon stream comprising pyrolysis plastic oil comprising the following steps:
   a) providing a hydrocarbon stream containing at least 10 wt % of pyrolysis plastic oil, the other part of said hydrocarbon stream being a first diluent, or alternatively providing a hydrocarbon stream containing only pyrolysis plastic oil;
   b) optionally putting in contact the hydrocarbon stream obtained at the step a) with silica gel, clays, alkaline or alkaline earth metal oxide, iron oxide, ion exchange resins, active carbon, active aluminum oxide, molecular sieves, alkaline oxide and/or porous supports containing lamellar double hydroxide modified or not and silica gel, or any mixture thereof to trap silicon and/or metals and/or phosphorous and/or halogenates trap, and/or water;
   c) performing a selective hydrogenation step at a temperature ranging from 25 to 225° C., a LHSV ranging from 1 to 10 h$^{-1}$, a pressure ranging from 5 to 90 barg so that the effluent obtained at the exit of said selective hydrogenation step has a diene value of at most 2.0 gI2/100 g as measured according to UOP 326;
   d) contacting the stream obtained at the step c), being optionally diluted with a second diluent, with a cracking catalyst being a 10 MR and/or 12 MR molecular sieve at a temperature ranging from 450° C. to 650° C., a total pressure ranging from 0.5 to 10 barg and/or with an hydrogen partial pressure ranging from 0 to 7.5 barg to crack the olefins and/or paraffins of said pyrolysis plastic oil into olefins having 2 to 4 carbon atoms;
   e) separating from the effluents obtained at the step d) a first stream containing olefins and saturated hydrocarbons having at most 3 carbon atoms, and a second stream containing hydrocarbons having 4 or more carbon atoms;
   f) recovering from said first stream the ethylene and propylene.

2. The process according to claim 1, wherein said pyrolysis plastic oil in said hydrocarbon stream has a starting boiling point of at least 15° C., and a final boiling point of at most 700° C.

3. The process according to claim 1, wherein said pyrolysis plastic oil has a diene value of at least 1.0, to at most 50 gI2/100 g as measured according to UOP 326, and/or contains more than 2 ppm wt of metals.

4. The process according to claim 1, wherein said hydrocarbon stream contains at least 25 wt % of said pyrolysis plastic oil and at most 100 wt % of said pyrolysis plastic oil.

5. The process according to claim 1, wherein said hydrocarbon stream contains only pyrolysis plastic oil, or alternatively said hydrocarbon stream contains at least 25 wt % of pyrolysis plastic oil, the other part of said hydrocarbon stream being a first diluent.

6. The process according to claim 1, wherein said first diluent is selected from an olefinic or paraffinic refinery or petrochemical stream including butenes, pyrolysis gasoline from a steam cracker, light cracked naphtha spirit from a FCC, coker naphtha from a coker, or a saturated hydrocarbon having a boiling range from 15 to 250° C. as measured with method ASTM D2887, or any combination thereof.

7. The process according to claim 1, wherein concerning said selective hydrogenation step of said hydrocarbon stream, one or more of the following statements is true:
the LHSV ranges from 1 to 6 $h^{-1}$;
the pressure ranges from 15-50 barg in presence of $H_2$, and/or the molar ratio of $H_2$ to the total molar sum of alkynes and dienes in said hydrocarbon stream is of at least 1.5, to at most 15;
said selective hydrogenation step is performed in one or more catalyst bed with an overall temperature increase of at most 150° C., and/or a temperature increase of at most 100° C., for each catalyst bed, with optionally intermediary quench between said catalyst beds, said quench being performed with $H_2$ or with the effluents of said selective hydrogenation step;
said first step is performed in a fixed bed reactor over a catalyst that comprises at least one metal of group VIII on a support selected from the group consisting of alumina, titania, silica, zirconia, magnesia, carbon and mixture thereof;
said first step can also be performed in a fixed bed reactor over a catalyst that comprises at least one metal of group VIB optionally in combination with a promotor selected from at least one metal of group VIII and/VIIIB these metals being used in sulfided form and optionally supported on alumina, titania, zirconia, silica, carbon and/or mixtures thereof; and/or
the effluents obtained at the exit of said selective hydrogenation step has a diene value of at most 1.5 g I2/100 g.

8. The process according to claim 1, wherein for said step d) of contacting the stream obtained at the previous step with a cracking catalyst one or more of the following statements is true:
temperature of cracking reaction ranges from 500 to 650° C.;
the cracking reaction is performed in a fixed bed reactor, or a moving bed reactor or a fluidized bed reactor;
the LHSV ranges from 1 to 30 $h^{-1}$;
the total pressure in the reactor ranges from 0.5 to 10 barg;
the cracking reaction is performed without hydrogen or hydrogen is present at a pressure of maximum 2.5 barg optionally in presence of dimethyl di sulfur at a concentration ranging from 50 to 300 ppm wt; and/or
the catalyst is selected from SAPO-5, and the like having an API structure, SAPO-41, and the like having an AFO structure, SAPO-11, and the like having an AEL structure, SAPO-37, and the like having a FAU structure with a silicon content ranging from 0.1 to 10 atom %, where the sum of Al+P+Si is 100, or MFI, for instance ZSM-5, silicalite-1, boralite C, TS-1; MEL, for instance ZSM-11, silicalite-2, boralite D, TS-2, SSZ-46; PER for instance Ferrierite, FU-9, ZSM-35; MTT for instance ZSM-23; MWW for instance MCM-22, PSH-3, ITQ-1, MCM-49; TON for instance ZSM-22, Theta-1, NU-10; EUO for instance ZSM-50, EU-1; MRS for instance ZSM-57; CON like CIT-1; and ZSM-48 family of microporous materials consisting of silicon, aluminium, oxygen and optionally boron.

9. The process according to claim 1, wherein said trap of step b) is a silica gel, activated carbon, activated aluminum oxide and/or molecular sieves working at a temperature ranging from 20 to 200° C. and/or a LHSV between 1 to 10$h^{-1}$, and/or a pressure ranging from 1 to 90 barg in presence of $H_2$ or in absence of $H_2$.

10. The process according to claim 1, wherein said pyrolysis plastic is originating directly, i.e. without further treatment or modification, from a waste plastic pyrolizer where waste plastic have been thermally pyrolyzed, or alternatively said pyrolysis plastic oil and/or said hydrocarbon stream of step a) is treated before step b) in one or more of the followed pre-treatment unit:
in a desalting unit to remove water-soluble salts;
in an impurities removal treatment step to remove silicon, phosphorous, metals and/or halogenated compounds, optionally via a solvent extraction or in a guard bed, said guard bed working at a temperature of at most 200° C., and/or a LHSV between 1 to 10 $h^{-1}$, and/or a pressure ranging from 1 to 90 barg either in presence of $H_2$ or in the absence of $H_2$;
in a separation unit to extract the particles and gums by filtration, centrifugation or a combination of the two technics; and/or
in a dewatering unit to remove water in said hydrocarbon stream to reach a water content of less than 0.1% vol according to ASTM D95.

11. The process according to claim 1, wherein after step e) hydrocarbons having 4 to 6 carbon atoms are separated from said second stream to be further cracked optionally by recycling them at step d).

12. The process according to claim 1, wherein the hydrocarbons having at least 7 carbon atoms are separated from said second stream, hydrogenated and/or hydrotreated and sent at least partially to a steam cracker to be cracked into olefins.

13. The process according to claim 1, wherein said process for purification comprises the preliminary step a1) of providing a waste plastic stream; a2) pyrolyzing said waste plastic stream at a temperature of at least 200° C.; a3) recovering a pyrolizer effluent and separating said pyrolizer effluent into a C1 to C4 hydrocarbons fraction, a fraction having a boiling range higher than 350° C. and a fraction being said pyrolysis plastic oil; a4) sending said fraction having a boiling range higher than 350° C. into a FCC, or an hydrocracking unit, a coker or a visbreaker or blending said fraction having a boiling range higher than 350° C. in crude oil or in a crude oil cut to be further refined.

14. The process according to claim 1, wherein the hydrocarbons having a boiling point higher than 350° C. are removed from said second stream and are further converted into a FCC, or an hydrocracking unit, a coker or a visbreaker or blended in crude oil or crude oil cut to be further refined.

15. The process according to claim 1, wherein said first diluent is selected from an olefinic refinery or petrochemical stream including butenes, pyrolysis gasoline from a steam cracker, light cracked naphtha spirit from a FCC, coker naphtha from a coker, or a saturated hydrocarbon having a boiling range from 15 to 250° C. as measured with method ASTM D2887, or any combination thereof.

16. The process according to claim 1, wherein said second diluent is incorporated at step d) so that the olefins content at the inlet step d) is at most 60 wt %, being an olefinic or paraffinic refinery stream.

17. The process according to claim 1, wherein said catalyst is a Ni based catalyst being a passivated after its reduction using di-alkyl-sulfide such as DiMethylSulfide (DMS) or DiEthylSulfide (DES) orthiophenic compounds.

18. The process according to claim 1, wherein the cracking catalyst is a crystalline silicate, metal containing crystalline silicate or a dealuminated crystalline silicate or any mixture thereof.

19. The process according to claim 1, wherein the cracking catalyst has a MFI or the MEL structure modified with the metals Mg, Ca, La, Ni, Ce, Zn, Co, Ag, Fe, Cu or Ga or mixtures thereof with a metal content of at least 0.1 wt % and at most 10 wt %.

20. The process according to claim 1, wherein said second diluent is a naphtha having a boiling range from 15 to 250° C. as measured with method ASTM D2887 or a saturated hydrocarbon solvent having a boiling range from 15 to 250° C. as measured with method ASTM D2887, or a part of said second stream recovered at step e), or N-pentane or iso-paraffinic solvent, or any mixture thereof.

* * * * *